United States Patent
Haining et al.

(10) Patent No.: US 11,179,480 B2
(45) Date of Patent: Nov. 23, 2021

(54) IN VIVO METHODS FOR IDENTIFYING CANCER-ASSOCIATED IMMUNOTHERAPY TARGETS

(71) Applicant: Dana-Farber Cancer Institute, Inc., Boston, MA (US)

(72) Inventors: William N. Haining, Newton, MA (US); Robert Manguso, Boston, MA (US); Natalie Collins, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 608 days.

(21) Appl. No.: 15/536,520

(22) PCT Filed: Dec. 22, 2015

(86) PCT No.: PCT/US2015/067308
§ 371 (c)(1),
(2) Date: Apr. 5, 2018

(87) PCT Pub. No.: WO2016/106295
PCT Pub. Date: Jun. 30, 2016

(65) Prior Publication Data
US 2017/0360963 A1   Dec. 21, 2017

Related U.S. Application Data

(60) Provisional application No. 62/095,271, filed on Dec. 22, 2014.

(51) Int. Cl.
| | | |
|---|---|---|
| *C12Q 1/68* | (2018.01) | |
| *A61K 49/00* | (2006.01) | |
| *G01N 33/50* | (2006.01) | |
| *G01N 33/574* | (2006.01) | |
| *A01K 67/027* | (2006.01) | |
| *A61K 35/12* | (2015.01) | |

(52) U.S. Cl.
CPC ........ *A61K 49/0008* (2013.01); *A01K 67/027* (2013.01); *A01K 67/0271* (2013.01); *G01N 33/5005* (2013.01); *G01N 33/5047* (2013.01); *G01N 33/574* (2013.01); *A01K 2207/12* (2013.01); *A01K 2267/0331* (2013.01); *A61K 35/12* (2013.01); *C12N 2740/15043* (2013.01); *C12N 2830/003* (2013.01)

(58) Field of Classification Search
CPC .. A61K 49/0008; A61K 35/12; A01K 67/027; A01K 67/0271; A01K 2207/12; A01K 2267/0331; G01N 33/5005; G01N 33/5047; G01N 33/574; C12N 2740/15043; C12N 2830/003
See application file for complete search history.

(56) References Cited

U.S. PATENT DOCUMENTS

2011/0286973 A1   11/2011   Serbedzija et al.

OTHER PUBLICATIONS

Soto-Pantoja et al in "CD47 in the Tumor Microenvironment Limits Cooperation between Antitumor T-cell Immunity and Radiotherapy", (Cancer Research Dec. 2014 vol. 74, No. 23, published online Oct. 8, 2014). (Year: 2014).*
Ferrantini et al., entitled 'alpha-interferon Gene Transfer into Metastatic Friend Leukemia Cells Abrogated Tumorigenicity in Immunocompetent Mice: Antitumor Therapy by Means of Interferon-producing Cells' (Cancer Res, vol. 53, No. 5, pp. 1107-1112, 1993, IDS reference) (Year: 1993).*
International Search Report and Written Opinion for International Application No. PCT/US15/67308 dated Apr. 13, 2016.
Ferrantini et al., "Alpha 1-interferon gene transfer into metastatic Friend leukemia cells abrogated tumorigenicity in immunocompetent mice: antitumor therapy by means of interferon-producing cells," Cancer Res, 53(5): 1107-1112 (1993).

* cited by examiner

*Primary Examiner* — Catherine S Hibbert
(74) *Attorney, Agent, or Firm* — Foley Hoag LLP

(57) ABSTRACT

The invention provides in vivo methods for identifying cancer-associated immunotherapy targets.

33 Claims, 7 Drawing Sheets

Specification includes a Sequence Listing.

IN VIVO METHODS FOR IDENTIFYING CANCER-ASSOCIATED IMMUNOTHERAPY TARGETS

CROSS-REFERENCE TO RELATED APPLICATIONS

This application claims the benefit of U.S. Provisional Application No. 62/095,271, filed on 22 Dec. 2014; the entire contents of said application are incorporated herein in their entirety by this reference.

BACKGROUND OF THE INVENTION

Classical methods of immunology for identifying genetic factors influencing immune responses to cancer cell detection and destruction have traditionally relied on stepwise analysis of individual gene targets. Systematic and large-scale analyses of potential immunomodulatory factors would be useful, particularly in identifying combinations of factors influencing immune responses to cancer. However, such analyses have been hampered by the lack of methods for identifying physiologically relevant genes expressed by cancer cells that impair the tumor-specific immune response. Accordingly, there is a great need in the art to identify such methods.

SUMMARY OF THE INVENTION

The present invention provides methods for overcoming the long-felt difficulties in identifying cancer-associated targets for immunotherapy based on in vivo screening immunocompetent or immunodeficient hosts transplanted with genetically modified cancer cells and treated with at least one immunotherapy.

In one aspect, an in vivo method of identifying a cancer cell modulator of response to an anti-cancer immunotherapy, comprising a) obtaining at least a first population of cancer cells, wherein the cancer cells are syngeneic to a first and second subject, wherein the first subject is immunocompetent and the second subject is immuno-incompetent; b) obtaining at least a second population of cancer cells, wherein the at least first population of cancer cells are genetically engineered to comprise at least one genetic modification; c) transplanting a portion of the second population of cancer cells into the first subject; d) administering at least one immunotherapy to the first subject; e) determining the representation of the at least one genetic modification from at least one population of cancerous cells propagated in the first subject from said transplanted portion of the second population of cancer cells relative to the representation of the at least one genetic modification from the portion of the second population of cancer cells prior to transplantation; f) repeating steps c) through e) with the second subject; and g) determining at least one genetic modification having a significantly modulated relative representation in the first subject and not having a significantly modulated relative representation in the second subject, thereby identifying a cancer cell modulator of response to an anti-cancer immunotherapy, is provided.

As described further herein, particular embodiments can be applied to any aspect of the present invention. For example, in one embodiment, the first population of cancer cells are solid tumor cancer cells. In another embodiment, the first population of cancer cells are hematological cancer cells. In still another embodiment, the first population of cancer cells is autologous to or congenic to the first or second subject. In yet another embodiment, the at least first population of cancer cells are human cancer cells and the first and second subjects are non-human animals. In another embodiment, the first and/or second subject is a vertebrate, such as a mammal, a non-human primate, a mouse, a rat, and a zebrafish.

In still another embodiment, the immunocompetent first subject is a wild type non-human animal. In yet another embodiment, the immune-incompetent second subject comprises at least one substantially reduced immunological function of at least one immune cell type relative to the immunocompetent first subject or wherein the immune-incompetent second subject is immunodeficient. In another embodiment, the at least one immune cell type is contacted with an agent that substantially reduces the at least one immunological function of the at least one immune cell type, such as an antibody, radiation, or chemotherapy. In still another embodiment, the at least one immune cell type is genetically engineered to substantially reduce the at least one immunological function of the at least one immune cell type. For example, the immune cell type is selected from the group consisting of B cells, T cells, CD8+ T cells, CD4+ T cells, regulatory T cells, macrophages, granulocytes, Natural Killer (NK) cells, and combinations thereof. In addition, the immune cells can be selected from the group consisting of resting, mitotic, terminally differentiated, post-mitotic, unactivated, and activated cells, and combinations thereof. In some embodiment, the immune cells have not been exogenously stimulated to divide.

In another embodiment, the at least first population of cells is contacted with a vector comprising an exogenous nucleic acid, wherein the vector 1) integrates into a chromosome or 2) exists as an extrachromosomal nucleic acid compartment of the cell, and expresses exogenous nucleic acids or proteins in the cell to generate the at least one genetic modification in the at least second population of cancer cells. In still another embodiment, a cell of the at least second population of cancer cells has a single vector comprising an exogenous nucleic acid. In yet another embodiment, the at least one vector is a viral vector. In another embodiment, the viral vector is a lentiviral vector. In still another embodiment, the viral vector expresses an exogenous nucleic acid. In yet another embodiment, the exogenous nucleic acid is selected from the group consisting of a nucleic acid barcode, an open reading frame, a tumor-associated mutation, mRNA, sgRNA, antisense RNA, shRNA, siRNA, microRNA, PiwiRNA, and combinations thereof. In another embodiment, the exogenous nucleic acid comprises a) an engineered, non-naturally occurring Clustered Regularly Interspaced Short Palindromic Repeats (CRISPR) guide RNA that hybridizes with a target nucleic acid sequence of interest and/or b) a nucleotide sequence encoding a Type-II Cas9 protein, optionally wherein the cells are transgenic for Cas9. In still another embodiment, the vector is inducible. In yet another embodiment, inducible expression is regulated using a doxycycline-inducible promoter. In another embodiment, the vector comprises a nucleic acid encoding a reporter, such as a fluorescent protein or a cell-surface protein. In still another embodiment, the reporter is used to identify and/or isolate the genetically modified cancer cells in the at least second population of cancer cells. In yet another embodiment, the portion of the second population of cancer cells transplanted into the first and/or second subject consists essentially of the isolated genetically modified cancer cells.

In another embodiment, the portion of the second population of cancer cells is focally transplanted to the first and/or second subject. In still another embodiment, the portion of the second population of cancer cells is systemically transplanted to the first and/or second subject. In yet another embodiment, the immunotherapy is administered concurrently with, before, or after the transplantation of the portion of the second population of cancer cells. In another embodiment, the at least one immunotherapy reduces but does not eliminate the portion of the second population of cancer cells. In still another embodiment, the at least one immunotherapy increases infiltration of lymphocytes into a solid tumor formed by the portion of the second population of cancer cells. In yet another embodiment, the at least one immunotherapy comprises at least one anti-immune checkpoint inhibitor, such as CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, HHLA2, butyrophilins, A2aR, or combinations thereof. In another embodiment, the at least one anti-immune checkpoint is selected from the group consisting of PD-1, PD-L1, PD-L2, CTLA-4, and combinations thereof.

In still another embodiment, the relative representation of the at least one genetic modification is determined by detecting nucleic acid markers, protein markers, and/or cellular markers of the cells comprising the at least one genetic modification. In another embodiment, the markers are detected by nucleic acid sequencing, next generation sequencing, flow cytometry, and immunodetection. In still another embodiment, a significant modulation in relative marker representation is at least a 1.5-fold difference. In yet another embodiment, the at least first population of cancer cells and the at least second population of cancer cells are co-cultured and the at least second population of cancer cells comprises at least a portion of the at least first population of cancer cells. In another embodiment, said at least second population of cancer cells has essentially an equal ratio of genetically modified and genetically unmodified cancer cells. In still another embodiment, a significant modulation in relative marker representation is at least a 1.5-fold difference. In yet another embodiment, a cancer cell modulator of response to an anti-cancer immunotherapy produced according to any method described herein.

DETAILED DESCRIPTION OF THE INVENTION

Figure 1:
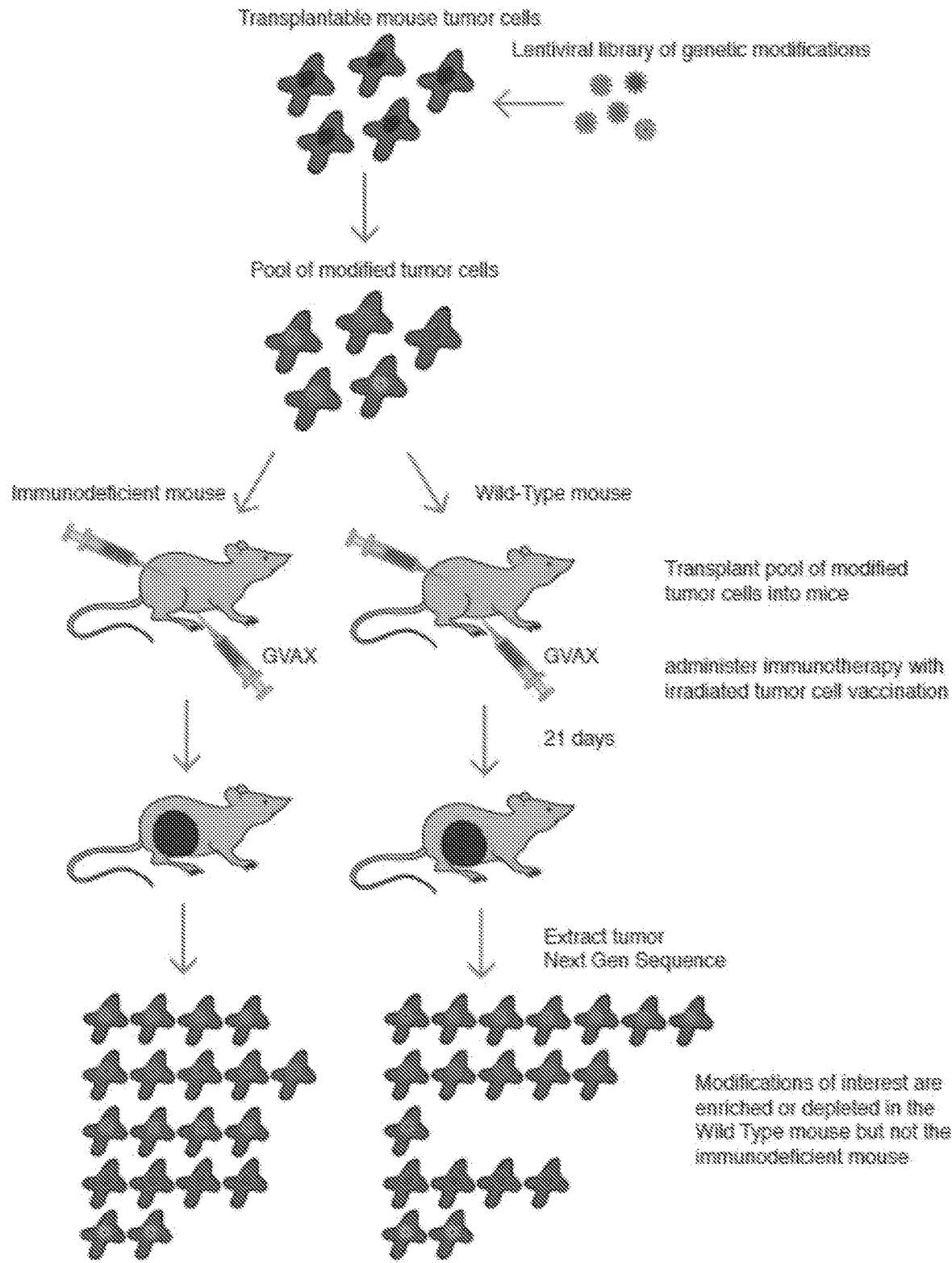
FIG. 1 shows a representative embodiment of an in vivo screening system for identifying cancer-associated immunotherapy targets. In the representative embodiment, transplantable mouse cancer lines are transduced in vitro with lentiviral libraries of bar coded genetic modifications (KO or overexpression). Transduced cells are selected and then injected subcutaneously into either WT or immunodeficient mice treated with some form of immunotherapy, such as irradiated GMCSF-expressing tumor cell vaccination (GVAX). Tumors form over a period of 21 days and are then extracted, dissociated, and genomic DNA is isolated from the tumor cells. Next generation sequencing is used to quantify the changes in representation of modifications in the population of cells from the input pool to the tumors after 21 days. By comparing the immunodeficient and immunocompetent conditions, modifications that specifically increase of decrease the susceptibility of tumor cells to immune attack are identified.
Figure 2:
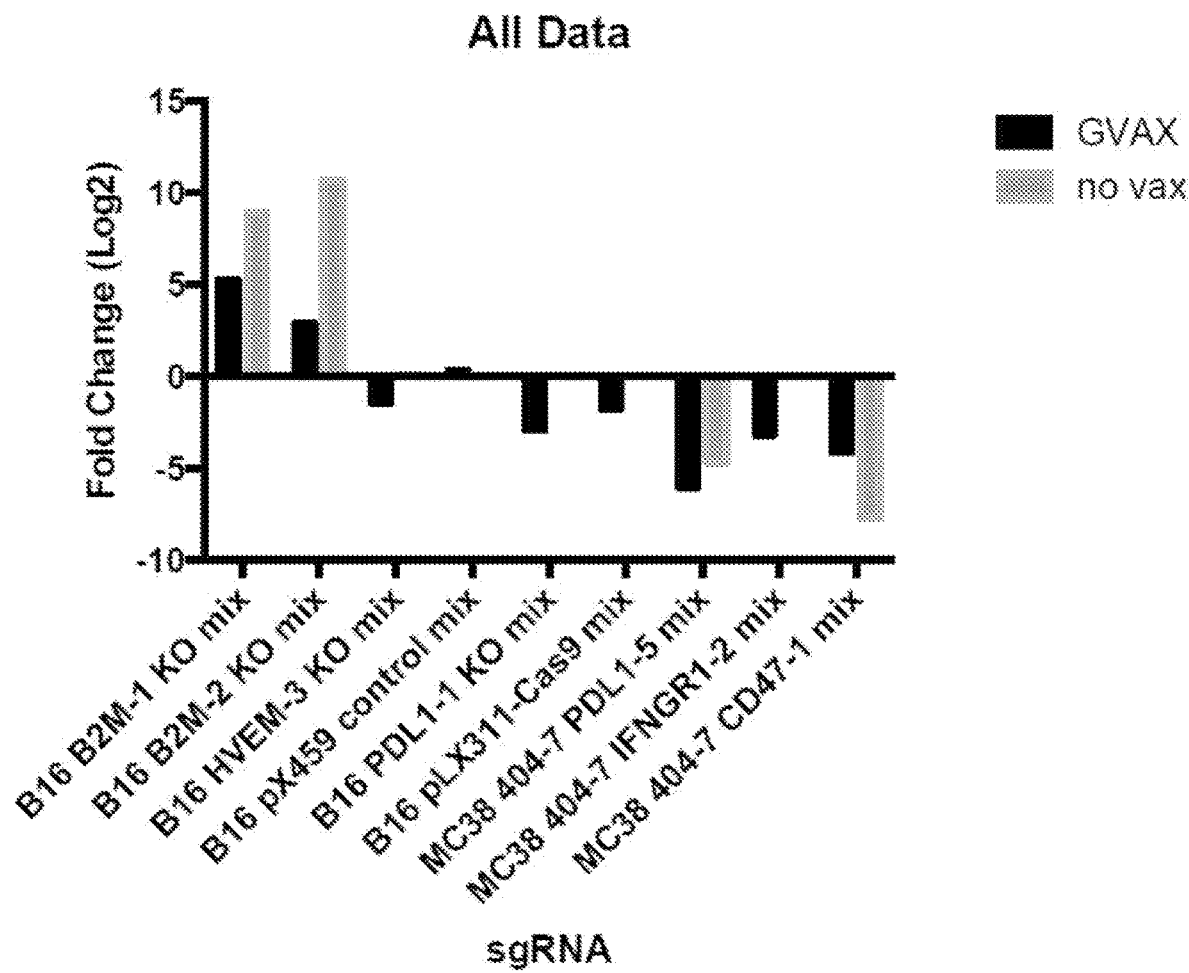
FIG. 2 shows the results of depleting genes relevant for tumor immunity in a competitive in vivo assay. MC38 colon carcinoma cells expressing an inducible version of Cas9 were transduced with guide RNAs for Beta-2 microglobulin, PD-L1, or a control guide RNA and mixed with WT CD19-expressing cells. The left panel shows the ratio of WT (CD19+) to modified (CD19−) cells after 21 days in culture. The right panel shows the same ratio after 21 days in immunocompetent animal treated with GVAX.
Figure 3:
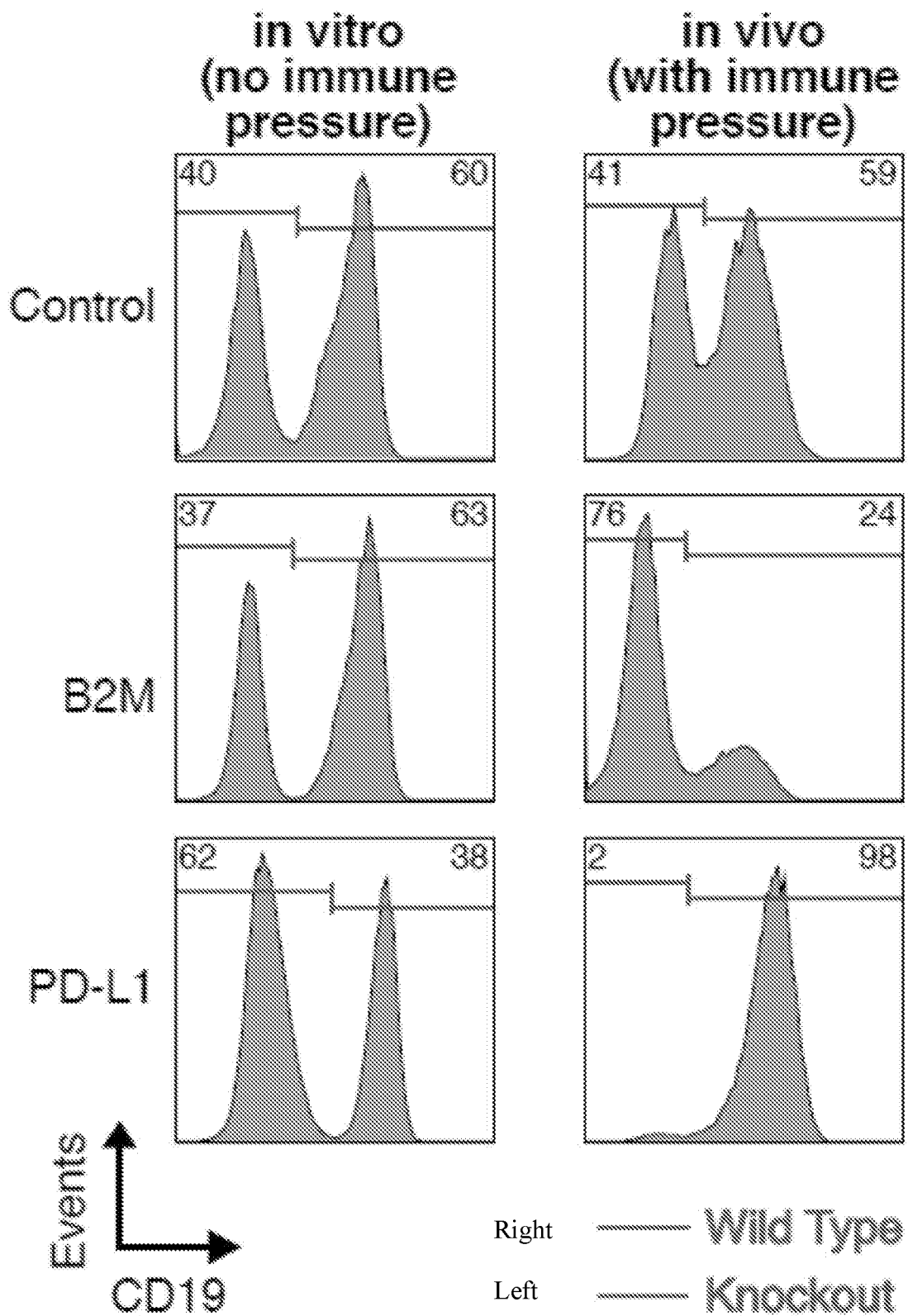
FIG. 3 shows that a competitive in vivo assay can detect immune-dependent advantages or disadvantages in multiple cell lines modified in different ways. The y-axis shows the $\log_2$ transformed fold enrichment or depletion of modified cells compared to WT cells in a mouse tumor. B16 cells were transiently transfected with a plasmid containing Cas9 and a guide RNA targeting B2M, PDL1, HVEM, or a control guide RNA. MC38 cells expressing an inducible Cas9 were lentivirally transduced with plasmids containing guide RNAs for PDL1, IFNGR1, and CD47. B16 constitutive Cas9-expressing cells were mixed with WT B16 cells (B16 pLX311-Cas9 mix). The depletion of the Cas9-expressing cells indicates that Cas9 may serve as a xeno-antigen. Results for wild type cells (labeled "right") correspond to the peak on the right side of each graph, whereas results for knockout cells (labeled "left") correspond to the peak on the left side of each graph.
Figure 4:
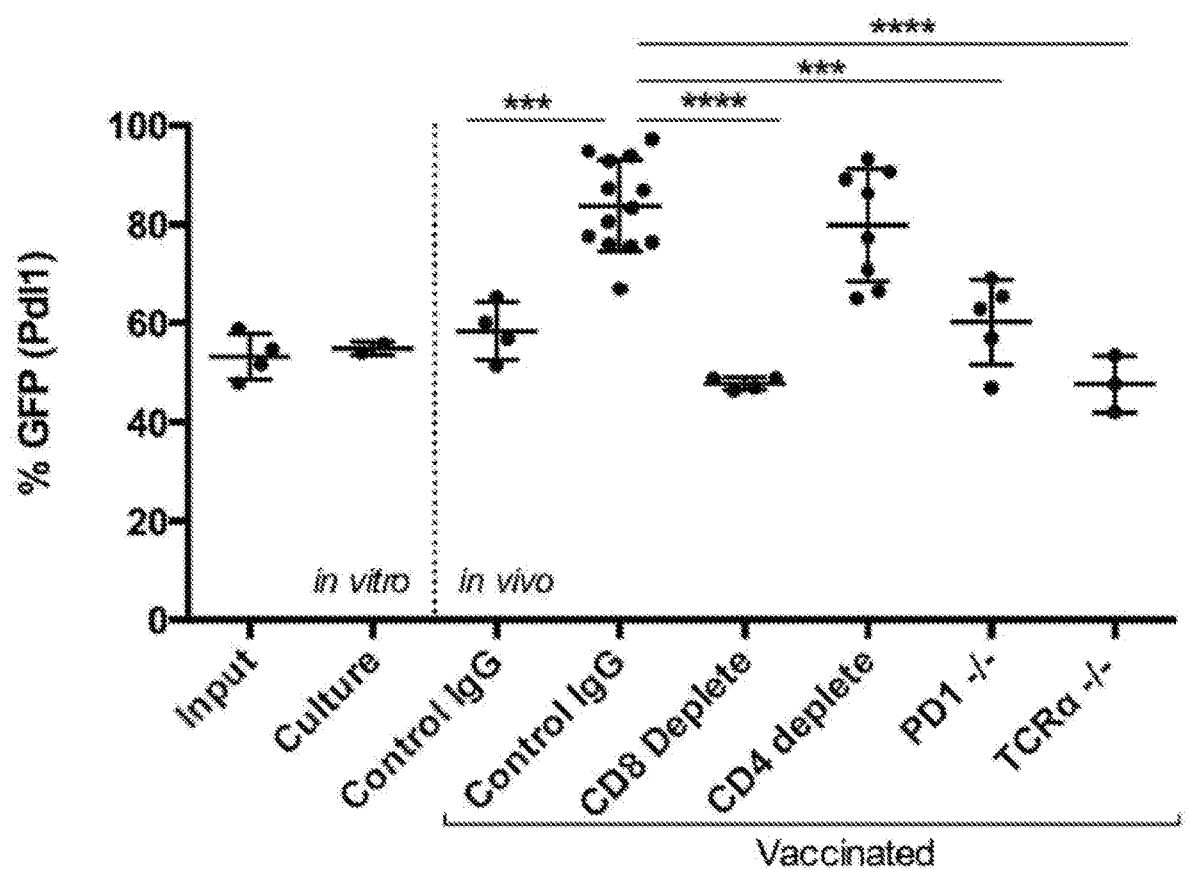
FIG. 4 shows that PD-L1 overexpression confers selective advantage under immune pressure that is dependent on functional CD8+ T cells and PD-1. B16 melanoma cells overexpressing PD-L1 were mixed at an equal ratio in a head to head competition assay with control LacZ expressing cells and injected into wild type, TCRalpha-deleted, or PD-1-deleted C57BL6/J animals, as indicated, to form subcutaneous tumors. Animals were treated with vaccination in combination with CD4+ or CD8+ T cell depletion to apply or remove immune pressure.
Figure 5:
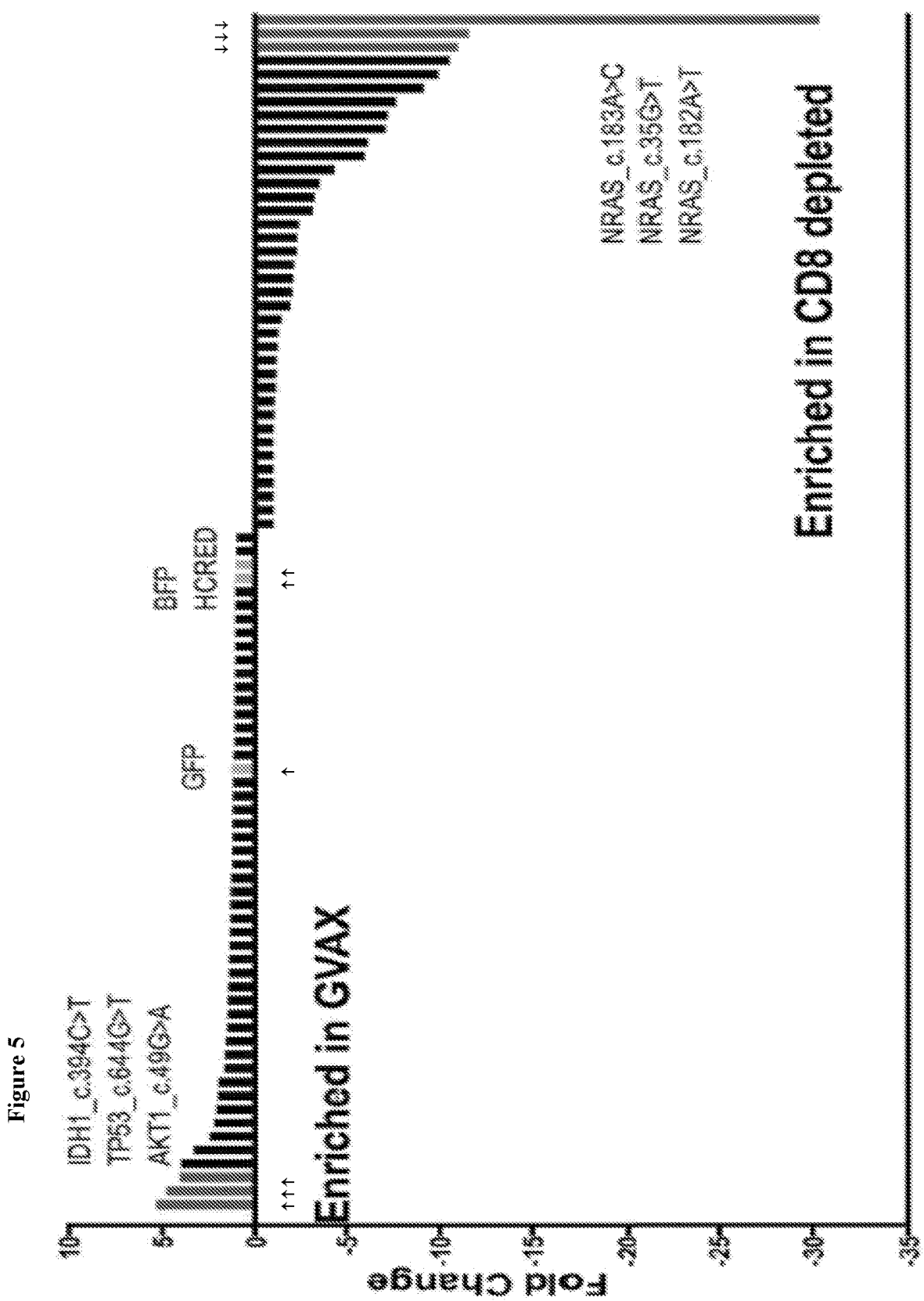
FIG. 5 shows the results of a tumor-associated mutation screen that identifies candidate immune inhibitory mutations. A pool of B16 melanoma expressing 96 tumor-associated mutations was injected into wild type C57BL6/J mice to form subcutaneous tumors. Tumor genomic DNA was sequenced at time of tumor injection and from resulting tumors after 12 days. Relative representation of mutations in resulting tumors from vaccinated animals compared to vaccination combined with CD8 depletion is shown. The listed mutations correspond to the three bars on the extreme ends of the graph indicated by arrows. The GFP, BFP, and HCRED control bars are also indicated by arrows.

The present invention is based in part on the discovery of methods allowing for the identification of genes expressed by cancer cells that mediate suppression of anti-tumor immunity and are thus targets for immunotherapy. The present invention overcomes numerous unsolved challenges in the art. For example, immune selective pressure while allowing for cancer cell retrieval without complete cancer cell eradication was determined to be modulated by the use of immunotherapy titration, timing, and cellular labeling. Moreover, high throughput analyses were determined using tags for genetically engineered loci, genetically engineered cancer cells (e.g., doxycycline-inducible Cas9-expressing cancer cell lines), and high throughput detection systems. Such methods allow for the identification and interrogation of combinations of factors regulating suppression of anti-tumor immunity in cancer cells.

A. Cancer Cells

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. In some embodiments, such cells exhibit such characteristics in part or in full due to the overexpression and/or underexpression of cancer cell-associated factors modulating the ability of immune cells to recognize, target, and/or neutralize the cancer cells. For example, cancer calls can express immune checkpoint proteins, such as PD-1, PD-L1, and/or CTLA-4. Cancer cells are often in the form of a solid mass (e.g., a tumor), but such cells may exist alone within an animal, such as in a body fluid, or may be a non-tumorigenic cancer cell, such as a leukemia cell. The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

As used herein, the term "cancer" includes premalignant, as well as malignant, cancers. The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia.

Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The methods described herein use genetically modified cancer cells, with or without genetically unmodified cancer cells, for transplantation into subjects. The cancer cells are at least syngeneic to the subject in order to maintain immunocompatibility during screening processes for the identification of cancer cell modulators of responses to an anti-cancer immunotherapy since cells derived from a donor subject having a similar immune background will avoid an adverse immunogenic response. The term "syngeneic" can refer to the state of deriving from, originating in, or being members of the same species that are genetically identical, particularly with respect to antigens or immunological reactions. These include identical twins having matching MHC types. Thus, a "syngeneic transplant" refers to transfer of cells from a donor to a recipient who is genetically identical to the donor or is sufficiently immunologically compatible as to allow for transplantation without an undesired adverse immunogenic response (e.g., such as one that would work against interpretation of immunological screen results described herein).

A syngeneic transplant can be "autologous" if the transferred cells are obtained from and transplanted to the same subject. An "autologous transplant" refers to the harvesting and reinfusion or transplant of a subject's own cells or organs. Exclusive or supplemental use of autologous cells may eliminate or reduce many adverse effects of administration of the cells back to the host, particular graft versus host reaction.

A syngeneic transplant can be "matched allogeneic" if the transferred cells are obtained from and transplanted to different members of the same species yet have sufficiently matched major histocompatibility complex (MHC) antigens to avoid an adverse immunogenic response. Determining the degree of MHC mismatch may be accomplished according to standard tests known and used in the art. For instance, there are at least six major categories of MHC genes in humans, identified as being important in transplant biology. HLA-A, HLA-B, HLA-C encode the HLA class I proteins while HLA-DR, HLA-DQ, and HLA-DP encode the HLA class II proteins. Genes within each of these groups are highly polymorphic, as reflected in the numerous HLA alleles or variants found in the human population, and differences in these groups between individuals is associated with the strength of the immune response against transplanted cells. Standard methods for determining the degree of MHC match examine alleles within HLA-B and HLA-DR, or HLA-A, HLA-B and HLA-DR groups. Thus, tests may be made of at least 4, and even 5 or 6 MHC antigens within the two or three HLA groups, respectively. In serological MHC tests, antibodies directed against each HLA antigen type are reacted with cells from one subject (e.g., donor) to determine the presence or absence of certain MHC antigens that react with the antibodies. This is compared to the reactivity profile of the other subject (e.g., recipient). Reaction of the antibody with an MHC antigen is typically determined by incubating the antibody with cells, and then adding complement to induce cell lysis (i.e., lymphocytotoxicity testing). The reaction is examined and graded according to the amount of cells lysed in the reaction (see, for example, Mickelson and Petersdorf (1999) *Hematopoietic Cell Transplantation*, Thomas, E. D. et al. eds., pg 28-37, Blackwell Scientific, Malden, Mass.). Other cell-based assays include flow cytometry using labeled antibodies or enzyme linked immunoassays (ELISA). Molecular methods for determining MHC type are well known and generally employ synthetic probes and/or primers to detect specific gene sequences that encode the HLA protein. Synthetic oligonucleotides may be used as hybridization probes to detect restriction fragment length polymorphisms associated with particular HLA types (Vaughn (2002) *Method. Mol. Biol. MHC Protocol.* 210:45-60). Alternatively, primers may be used for amplifying the HLA sequences (e.g., by polymerase chain reaction or ligation chain reaction), the products of which may be further examined by direct DNA sequencing, restriction fragment polymorphism analysis (RFLP), or hybridization with a series of sequence specific oligonucleotide primers (SSOP) (Petersdorf et al. (1998) *Blood* 92:3515-3520; Morishima et al. (2002) *Blood* 99:4200-4206; and Middleton and Williams (2002) *Method. Mol. Biol. MHC Protocol.* 210:67-112).

A syngeneic transplant can be "congenic" if the transferred cells and cells of the subject differ in defined loci, such as a single locus, typically by inbreeding. The term "congenic" refers to deriving from, originating in, or being members of the same species, where the members are genetically identical except for a small genetic region, typically a single genetic locus (i.e., a single gene). A "congenic transplant" refers to transfer of cells or organs from a donor to a recipient, where the recipient is genetically identical to the donor except for a single genetic locus. For example, CD45 exists in several allelic forms and congenic mouse lines exist in which the mouse lines differ with respect to whether the CD45.1 or CD45.2 allelic versions are expressed.

By contrast, "mismatched allogeneic" refers to deriving from, originating in, or being members of the same species having non-identical major histocompatibility complex (MHC) antigens (i.e., proteins) as typically determined by standard assays used in the art, such as serological or molecular analysis of a defined number of MHC antigens, sufficient to elicit adverse immunogenic responses. A "partial mismatch" refers to partial match of the MHC antigens tested between members, typically between a donor and recipient. For instance, a "half mismatch" refers to 50% of the MHC antigens tested as showing different MHC antigen type between two members. A "full" or "complete" mismatch refers to all MHC antigens tested as being different between two members.

Similarly, in contrast, "xenogeneic" refers to deriving from, originating in, or being members of different species, e.g., human and rodent, human and swine, human and chimpanzee, etc. A "xenogeneic transplant" refers to transfer of cells or organs from a donor to a recipient where the recipient is a species different from that of the donor.

Cancer cells of interest may be obtained from and transplanted to any source or subject having an immune system. In one embodiment, the source or subject is a vertebrate, such as a mammal, including humans. As used herein, the terms "mammal" and "mammalian" refer to any vertebrate animal, including monotremes, marsupials and placental, that suckle their young and either give birth to living young (eutharian or placental mammals) or are egg-laying (metatharian or nonplacental mammals). Representative, non-limiting examples of non-human vertebrates include non-human primates (e.g., monkeys and chimpanzees), rodents (e.g., rats, mice, and guinea pigs), rabbits, canines, felines, birds, fish (e.g., zebrafish), and ruminants (e.g., cows, sheep, pigs, and horses). In one embodiment, the source or subject is a human (e.g., cells and/or a host having a defined genetic background or unknown genetic background may be obtained from a human for use in the methods of the present invention).

Cells may be obtained from a single source or a plurality of sources (e.g., a single subject or a plurality of subjects). A plurality refers to at least two (e.g., more than one). In still another embodiment, the non-human mammal is a mouse. The animals from which cell types of interest are obtained may be adult, newborn (e.g., less than 48 hours old), immature, or in utero. Cell types of interest may be primary cells, stem cells, established cancer cell lines, immortalized primary cells, and the like. In certain embodiments, the immune systems of host subjects can be engineered or otherwise elected to be immunological compatible with transplanted cancer cells. For example, in one embodiment, the subject may be "humanized" in order to be compatible with human cancer cells. The term "immune-system humanized" refers to an animal, such as a mouse, comprising human HSC lineage cells and human acquired and innate immune cells, survive without being rejected from the host animal, thereby allowing human hematopoiesis and both acquired and innate immunity to be reconstituted in the host animal. Acquired immune cells include T cells and B cells. Innate immune cells include macrophages, granulocytes (basophils, eosinophils, neutrophils), DCs, NK cells and mast cells. Representative, non-limiting examples include SCID-hu, Hu-PBL-SCID, Hu-SRC-SCID, NSG (NOD-SCID IL2r-gamma(null) lack an innate immune system, B cells, T cells, and cytokine signaling), NOG (NOD-SCID IL2r-gamma(truncated)), BRG (BALB/c-Rag2(null)IL2r-gamma(null)), and H2dRG (Stock-H2d-Rag2(null)IL2r-gamma(null)) mice (see, for example, Shultz et al. (2007) *Nat. Rev. Immunol.* 7:118; Pearson et al. (2008) *Curr. Protocol. Immunol.* 15:21; Brehm et al. (2010) *Clin. Immunol.* 135:84-98; McCune et al. (1988) *Science* 241:1632-

1639, U.S. Pat. No. 7,960,175, and U.S. Pat. Publ. 2006/0161996), as well as related null mutants of immune-related genes like Rag1 (lack B and T cells), Rag2 (lack B and T cells), TCR alpha (lack T cells), perforin (cD8+ T cells lack cytotoxic function), FoxP3 (lack functional CD4+ T regulatory cells), IL2rg, or Prf1, as well as mutants or knockouts of PD-1, PD-L1, Tim3, and/or 2B4, allow for efficient engraftment of human immune cells in and/or provide compartment-specific models of immunocompromised animals like mice (see, for example, PCT Publ. WO2013/062134). In addition, NSG-CD34+ (NOD-SCID IL2r-gamma(null) CD34+) humanized mice are useful for studying human gene and tumor activity in animal models like mice.

As used herein, "obtained" from a biological material source means any conventional method of harvesting or partitioning a source of biological material from a donor. For example, biological material may obtained from a solid tumor, a blood sample, such as a peripheral or cord blood sample, or harvested from another body fluid, such as bone marrow or amniotic fluid. Methods for obtaining such samples are well known to the artisan. In the present invention, the samples may be fresh (i.e., obtained from a donor without freezing). Moreover, the samples may be further manipulated to remove extraneous or unwanted components prior to expansion. The samples may also be obtained from a preserved stock. For example, in the case of cell lines or fluids, such as peripheral or cord blood, the samples may be withdrawn from a cryogenically or otherwise preserved bank of such cell lines or fluid. Such samples may be obtained from any suitable donor.

The obtained populations of cells may be used directly or frozen for use at a later date. A variety of mediums and protocols for cryopreservation are known in the art. Generally, the freezing medium will comprise DMSO from about 5-10%, 10-90% serum albumin, and 50-90% culture medium. Other additives useful for preserving cells include, by way of example and not limitation, disaccharides such as trehalose (Scheinkonig et al. (2004) *Bone Marrow Transplant.* 34:531-536), or a plasma volume expander, such as hetastarch (i.e., hydroxyethyl starch). In some embodiments, isotonic buffer solutions, such as phosphate-buffered saline, may be used. An exemplary cryopreservative composition has cell-culture medium with 4% HSA, 7.5% dimethyl sulfoxide (DMSO), and 2% hetastarch. Other compositions and methods for cryopreservation are well known and described in the art (see, e.g., Broxmeyer et al. (2003) *Proc. Natl. Acad. Sci. U.S.A.* 100:645-650). Cells are preserved at a final temperature of less than about −135° C.

B. Vectors Comprising Exogenous Nucleic Acid

The cancer cells described herein can be genetically engineered using standard recombinant techniques. The term "genetically engineered" refers to any manipulation that alters the nucleic acid sequence of a host cell. In some embodiments, such techniques use vectors, preferably expression vectors, containing one or more exogenous nucleic acid sequences. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of exogenous nucleic acid sequences to which they are operably linked. In general, expression vectors of utility in recombinant DNA techniques are often in the form of plasmids (vectors). However, the present invention is intended to include such other forms of expression vectors, such as viral vectors (e.g., lentiviruses, replication defective retroviruses, adenoviruses and adeno-associated viruses), which serve equivalent functions.

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40.

Vector DNA can be introduced into cancer cells via conventional transformation, transfection, or transduction techniques. As used herein, the terms "transformation" and "transfection" and "Transduction" are intended to refer to a variety of art-recognized techniques for introducing foreign nucleic acid into a host cell, including calcium phosphate or calcium chloride co-precipitation, DEAE-dextran-mediated transfection, lipofection, electroporation, or viral infection. Suitable methods for transforming, transfecting, or transducing host cells are well known in the art.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

Recombinant expression vectors can comprise an exogenous nucleic acid of interest in a form suitable for expression of the exogenous nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells, at particular times, etc. It will be appreciated by those skilled in the art that the design of the expression vector can depend on such factors as the choice of the host cell to be transformed, the level of exogenous nucleic acid and/or protein expression desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., E. coli) or eukaryotic cells (e.g., insect cells {using baculovirus expression vectors}, yeast cells or mammalian cells).

a) Exogenous Nucleic Acid

The vectors comprise exogenous nucleic acid. By "exogenous nucleic acid" or "exogenous nucleic acid" is meant any nucleotide sequence, particularly a DNA sequence, that is not normally present in the host cancer cell. By not normally present is meant that the sequence per se is not generally present in the host cancer cell or that a sequence that may normally be present is engineered to be present in a modified form, copy number, activity level, expression level, and the like. In one embodiment, the exogenous nucleic acid can be integrated into one or more chromosomes or be maintained as an extrachomosomal nucleic acid depot of a host cell by human intervention, such as by the methods of the present invention.

In one embodiment, a exogenous nucleic acid is an "RNA coding region." The RNA can be functional in and of itself, such as a ribozyme, or can represent a "gene of interest" or "open reading frame" encoding a polypeptide of interest, such as a Type-II CAS9 enzyme. In other embodiments the exogenous nucleic acid may be a nucleotide sequence, preferably a DNA sequence, that is used to mark the chromosome where it has integrated or may indicate a position where nucleic acid editing, such as by the CRSPR-CAS system, may occur. In this situation, the exogenous nucleic acid does not have to comprise a gene that encodes a protein that may be expressed.

A "gene of interest" is a nucleic acid sequence that encodes a protein or other molecule, such as an RNA or targeting nucleic acid sequence, that is desirable for maintenance and expression in a host cell. The gene of interest may be 1, 2, 3, 4, 5, 6, 7, 8, 9, 10, or more genes of interest, expressed from the same or different vectors. Similarly, the host cell can encompass 1, 2, 3, 4, 5, 6, 7, 8, 9, 10, or more copies of the same and/or different vectors (e.g., only a single integration of a single lentiviral expression vector, a single integration of each of several lentiviral expression vectors, multiple integrations of a single lentiviral expression vector, multiple integrations of each of several lentiviral expression vectors, and the like). In one embodiment, the gene of interest is useful for overexpressing and/or enhancing the activity of a nucleic acid or protein of interest. For example, the gene of interest may encode a protein or other molecule the expression of which is desired in the host cell. Such protein-encoding nucleic acid sequences are not particularly limited and are selected based on the desired exogenous perturbation desired. Thus, the gene of interest includes any gene that the skilled practitioner desires to have integrated and/or expressed. For example, exogenous expression of proteins related to autoimmune, allergic, vaccination, immunotolerance, cancer immunotherapy, immune exhaustion, immunological memory, or immunological epitope responses may be used. The gene of interest encode a protein or be a nucleic acid that serves as a marker to identify cells of interest or transduced cells. The gene of interest may encode a protein that modifies a physical characteristic of the transduced cell, such as a protein that modifies size, growth, or eventual tissue composition. In another example, the gene of interest may encode a protein of commercial value that may be harvested. Generally, the gene of interest is operatively linked to other sequences that are useful for obtaining the desired expression of the gene of interest, such as transcriptional regulatory sequences like inducible promoters, as described further below.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript. In some embodiments, an exogenous nucleic acid can comprise only a portion of a nucleic acid sequence, wherein the full length nucleic acid sequence comprises a full-length polypeptide or other marker of interest. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the present invention. The probe comprises a label group attached thereto, e.g., a radioisotope, a fluorescent compound, an enzyme, or an enzyme co-factor.

In some embodiments, genes of interest vary from wild type nucleic acid sequences due to degeneracy of the genetic code, from the nucleotide sequence of nucleic acid molecules encoding a protein which corresponds to a marker of interest, and thus encode the same protein, are also contemplated. Similarly, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. For example, in one embodiment, identified alleles of cancer-associated nucleic acid sequences of interest can be engineered into cancer cells to be screened. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative splicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

In one embodiment, an exogenous nucleic acid can be at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more identical to a wild type nucleic acid sequence, or to a wild type polypeptide encoded by such a nucleic acid sequence.

In still another embodiment, an exogenous nucleic acid can be at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, nucleic acid sequences encoding a polypeptide of interest that contain changes in amino acid residues that are not essential for activity. Such polypeptides differ in amino acid sequence from the naturally-occurring proteins which correspond to the markers of the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of antisense nucleic acid molecules, i.e., molecules which are complementary to a sense nucleic acid of a target, e.g., complementary to the coding strand of a double-stranded cDNA molecule or complementary to a target mRNA sequence. An antisense nucleic acid can hydrogen bond to (i.e. anneal with) a sense nucleic acid of the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the present invention. The non-coding regions ("5' and 3' untranslated regions") are the 5' and 3' sequences which flank the coding region and are not translated into amino acids.

Genes of interest may be nucleic acids themselves or encode a polypeptide, a naturally-occurring binding partner of a target of interest, an antibody against a target of interest, a combination of antibodies against a target of interest and antibodies against other immune-related targets, an agonist or antagonist of a target of interest, a peptidomimetic of a target of interest, a peptidomimetic of a target of interest, a small RNA directed against or a mimic of a target of interest, and the like. Such modulators are well known in the art and include, for example, an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule such as a Piwi RNA, triplex oligonucleotide, ribozyme, coding sequence for a target of interest. Such agents modulate the expression and/or activity of target biomolecules, which includes any decrease in expression or activity of the target biomolecule of at least about 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more as compared to the expression or activity of the target biomolecule which has not been targeted by a modulating agent.

In one embodiment, the vector and/or host cell may be engineered to express the CRISPR-Cas system for precise editing of genomic nucleic acids (e.g., for creating null mutations). In such embodiments, the CRISPR guide RNA and/or the Cas enzyme may be expressed. For example, a vector containing only the guide RNA (sgRNA) can be administered to an animal or cells transgenic for the Cas9 enzyme. Such strategies are well known in the art (see, for example, U.S. Pat. Nos. 8,697,359, 8,771,945, and 8,795,965, U.S. Pat. Publs. 2014/02730371, 2014/0234972, 2014/0273226, 2014/0227787, 2014/0248702, 2013/0288251, 2014/027230, and 2014/0273233; and PCT Pat. Publs. WO 2014/093701 and WO 2014/093595). Similar strategies may be used (e.g., designer zinc finger, transcription activator-like effectors (TALEs) or homing meganucleases). Such systems are well known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326:1509-1512; Moscou and Bogdanove (2009) *Science* 326:1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47).

In another embodiment, the gene of interest is useful for inhibiting the expression and/or activity of a nucleic acid or protein of interest. For example, target biomolecule expression and/or activity, such as an RNA coding region, may be reduced or inhibited using inhibitory RNAs. An "RNA coding region" is a nucleic acid that may serve as a template for the synthesis of an RNA molecule, such as an siRNA. "RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see, for example, Coburn and Cullen (2002) *J. Virol.* 76:9225), thereby inhibiting expression of the target biomarker nucleic acid. In one embodiment, the RNA coding region is a DNA sequence. The ability to down-regulate a target gene has many therapeutic and research applications, including identifying the biological functions of particular genes. Moreover, such inhibition may be achieved in screening assays that take advantage of pooling techniques, whereby groups of 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more, or any number or range in between, of RNA inhibitory agents, either co-expressed from the same vector or more than one vector, are transduced into cells of interest. Suitable inhibitory RNAs include, but are not limited to siRNAs, shRNAs, miRNAs, Piwis, dicer-substrate 27-mer duplexes, single-stranded interfering RNA, and the like. In particular, the combination of RNA inhibitory technology and lentiviruses as a tool for a gene specific knock-down in animal models is well known in the art (see, for example, U.S. Pat. Publ. 2005/0251872; EP Pat. Publ. 2166107; PCT Publs. WO 2004/022722 and 2007/109131; Tiscornia et al. (2003) *Proc. Natl. Acad. Sci. U.S.A.* 100:1844-1848; Rubinson et al. (2003) *Nat. Genet.* 33:401-406; and Dann et al. (2006) *Proc. Natl. Acad. Sci. U.S.A.* 103:11246-11251). As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 10%, 20%, 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

siRNAs typically refer to a double-stranded interfering RNA unless otherwise noted. In various embodiments, suitable siRNA molecules include double-stranded ribonucleic acid molecules comprising two nucleotide strands, each strand having about 19 to about 28 nucleotides (i.e. about 19, 20, 21, 22, 23, 24, 25, 26, 27, or 28 nucleotides). Thus, the phrase "interfering RNA having a length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

In addition to siRNA molecules, other interfering RNA molecules and RNA-like molecules may be used. Examples of other interfering RNA molecules that may to inhibit target biomolecules include, but are not limited to, short hairpin RNAs (shRNAs), single-stranded siRNAs, microRNAs (miRNAs), piwiRNA, dicer-substrate 27-mer duplexes, and variants thereof containing one or more chemically modified nucleotides, one or more non-nucleotides, one or more deoxyribonucleotides, and/or one or more non-phosphodiester linkages. Typically, all RNA or RNA-like molecules that may interact with transcripts RISC complexes and participate in RISC-related changes in gene expression may be referred to as "interfering RNAs" or "interfering RNA molecules."

Suitable interfering RNAs may readily be produced based on the well-known nucleotide sequences of target biomolecules. In various embodiments interfering RNAs that inhibit target biomolecules may comprise partially purified RNA, substantially pure RNA, synthetic RNA, recombinantly produced RNA, as well as altered RNA that differs from naturally-occurring RNA by the addition, deletion, substitution, and/or alteration of one or more nucleotides. Such alterations may include, for example, addition of non-nucleotide material, such as to the end(s) of the interfering RNAs or to one or more internal nucleotides of the interfering RNAs, including modifications that make the interfering RNAs resistant to nuclease digestion. Such alterations result in sequences that are generally at least about 80%, 81%, 82%, 83%, 84%, 85%, 86%, 87%, 88%, 89%, 90%, 91%, 92%, 93%, 94%, 95%, 96%, 97%, 98%, 99%, 99.5%, or more, or 100% identical to the sequence of the target biomolecule. When the gene to be down regulated is in a family of highly conserved genes, the sequence of the duplex region may be chosen with the aid of sequence comparison to target only the desired gene. On the other hand, if there is sufficient identity among a family of homologous genes within an organism, a duplex region may be designed that would down regulate a plurality of genes simultaneously.

In various embodiments one or both strands of the interfering RNAs may comprise a 3' overhang. As used herein, a "3' overhang" refers to at least one unpaired nucleotide extending from the 3'-end of an RNA strand. Thus in one embodiment, the interfering RNAs comprises at least one 3' overhang of from 1 to about 6 nucleotides (which includes ribonucleotides or deoxynucleotides) in length, from 1 to about 5 nucleotides in length, from 1 to about 4 nucleotides in length, or about 2 to about 4 nucleotides in length. In an illustrative embodiment in which both strands of the interfering RNAs molecule comprise a 3' overhang, wherein the length of the overhangs may be the same or different for each strand. In certain embodiments the 3' overhang is present on both strands of the interfering RNAs and is one, two, or three nucleotides in length. For example, each strand of the interfering RNAs may comprise 3' overhangs of dithymidylic acid ("TT") or diuridylic acid ("uu").

In order to enhance the stability of the interfering RNAs, the 3' overhangs may be also stabilized against degradation. In one embodiment, the overhangs are stabilized by including purine nucleotides, such as adenosine or guanosine nucleotides. In certain embodiments, substitution of pyrimidine nucleotides by modified analogues, e.g., substitution of uridine nucleotides in the 3' overhangs with 2'-deoxythymidine, is tolerated and does not affect the efficiency of RNA interference degradation. In particular, it is believed the absence of a 2' hydroxyl in the 2'-deoxythymidine may significantly enhance the nuclease resistance of the 3' overhang.

Interfering RNAs may be expressed from a vector described herein either as two separate, complementary RNA molecules, or as a single RNA molecule with two complementary regions. Selection of vectors suitable for expressing interfering RNAs, methods for inserting nucleic acid sequences for expressing the interfering RNAs into the vector, and methods of delivering the recombinant plasmid to the cells of interest are well known in the art (Tuschl (2002) *Nat. Biotechnol.* 20: 446-448; Brummelkamp et al. (2002) *Science* 296:550 553; Miyagishi et al. (2002) *Nat. Biotechnol.* 20:497-500; Paddison et al. (2002) *Genes Dev.* 16:948-958; Lee et al. (2002) *Nat. Biotechnol.* 20:500-505; and Paul et al. (2002) *Nat. Biotechnol.* 20:505-508).

In certain embodiments, the interfering RNAs may be delivered as a small hairpin RNA or short hairpin RNA (shRNA) (see, for example, U.S. Pat. Nos. 8,697,359 and 8,642,569). shRNA is a sequence of RNA that makes a tight hairpin turn that may be used to silence gene expression via RNA interference. In typical embodiments, shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA that is bound to it.

In certain embodiments, the sense sequence of the shRNA will be from about 19 to about 30, more nucleotides (e.g. about 19, 20, 21, 22, 23, 24, 25, 26, 27, 28, 29, or 30 nucleotides) in length, more typically from about 19 to about 22 nucleotides in length, the antisense sequence will be from about 19 to about 30, more typically from 19 to about 22 nucleotides (e.g. about 19, 20, 21 or 22 nucleotides), in length, and the loop region will be from about 3 to about 19 nucleotides (e.g., about 3, 4, 5, 6, 7, 8, 9, 10, 11, 12, 13, 14, 15, 16, 17, 18, and 19 nucleotides) in length. In some embodiments, the sense and antisense sequences are the same length, i.e. the shRNA will form a symmetrical hairpin, but this is not necessarily the case. In some cases, the sense or antisense strand may be shorter than its complementary strand, and an asymmetric hairpin is formed. Further, while in some instances the base pairing between the sense and antisense sequences is exact, this also need not be the case. Thus, some mismatch between the sequences may be tolerated, or even desired, e.g. to decrease the strength of the hydrogen bonding between the two strands. However, in one illustrative embodiment, the sense and antisense sequences are the same length, and the base pairing between the two is exact and does not contain any mismatches. The shRNA molecule may also comprise a 5'-terminal phosphate group that may be chemically modified. In addition, the loop portion of the shRNA molecule may comprise, for example, nucleotides, non-nucleotides, linker molecules, conjugate molecules, etc.

In certain embodiments, the PIWI RNA pathway is used to provide inhibition of target biomolecules. Piwi-interacting RNAs (piRNAs) were identified through association with Piwi proteins in mammalian testes (Aravin et al. (2006); Girard et al. (2006); Grivna et al. (2006); Lau et al. (2006). piRNAs and methods of making and using same to target and degrade nucleic acids are well known in the art (see, for example, U.S. Pat. Publ. 2011-0207625). These RNAs range from 26-30 nucleotides in length and are produced from discrete loci. Generally, genomic regions spanning 50-100 kB in length give rise to abundant piRNAs with profound strand asymmetry. Although the piRNAs themselves are not conserved, even between closely related species, the positions of piRNA loci in related genomes are conserved, with virtually all major piRNA-producing loci having syntenic counterparts in mice, rats and humans (Girard et al. (2006)). The loci and consequently the piRNAs themselves are relatively depleted of repeat and transposon sequences, with only 17% of human piRNAs corresponding to known repetitive elements as compared to a nearly 50% repeat content for the genome as a whole. In certain embodiments, methods are provided for inhibiting such targets in a cell, comprising administering an effective amount of a siRNA/shRNA/piwiRNA to the cell, such that target mRNA is degraded.

As described below, internal promoters may be engineered into vectors in order to allow for the independent expression of more than one gene of interest. If a second or additional gene of interest is included, an internal ribosomal entry site (IRES) sequence may be included (see, for example, U.S. Pat. No. 4,937,190). The IRES sequence may facilitate the expression of the reporter gene and may be used to create multigene, or polycistronic, messages. IRES elements are able to bypass the ribosome scanning model of 5'-methylated cap-dependent translation and begin translation at internal sites (Pelletier and Sonenberg, 1988). IRES elements are well known in the art and be isolated from, for example, at least two members of the picornavirus family (polio and encephalomyocarditis) have been described (Pelletier and Sonenberg, 1988), as well as from a mammalian message (Macejak and Sarnow, 1991). IRES elements may be linked to heterologous open reading frames. Multiple open reading frames may be transcribed together, each separated by an IRES, creating polycistronic messages. By virtue of the IRES element, each open reading frame is accessible to ribosomes for efficient translation. Multiple genes may be efficiently expressed using a single promoter/enhancer to transcribe a single message.

In certain embodiments of the invention, cells contacted with and encompassing vectors may be identified in vitro or in vivo by including a marker in the expression vector. Such markers would confer an identifiable change to the transduced cell permitting easy identification of cells containing the expression vector. For example, a gene of interest encoding a marker protein or a nucleic acid barcode (i.e., a unique nucleic acid sequence facilitating identification and associated with a specific gene of interest) may be engineered along with the primary gene of interest that is, for example, an RNA interfering nucleic acid, to allow for identification of cells that are expressing the desired protein.

Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker. Usually the inclusion of a drug selection marker aids in the cloning and identification of transformants, for example, genetic constructs that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Many useful reporter markers are known and include, for example, a fluorescence marker, preferably selected from green fluorescent protein (GFP), enhanced GFP (eGFP), DsRed, AsRed, HcRed, Tomatoe, Cherry, Katushka, and variants thereof (see, for example, U.S. Pat. Nos. 5,487,932 and 5,464,763). Examples of other useful reporters include various enzymes, prosthetic groups, fluorescent materials, luminescent materials, bioluminescent materials, and radioactive materials. In one embodiment, expression of cell surface markers, such as CD19, can be used to cellular detection, sorting, purification, identification, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In some embodiments, isolated nucleic acids are used in the genetic engineering process. An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

An exogenous nucleic acid can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

An exogenous nucleic acid can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

b) Viral Vectors

In some embodiments, viral vectors are preferable, especially those capable of stable integration into a host chromosome. In general, viral vectors are plasmid-based or virus-based, and are configured to carry the essential sequences for incorporating foreign nucleic acid, for selection and for transfer of the nucleic acid into a host cell. The viral construct is a nucleotide sequence that comprises sequences necessary for the production of recombinant retrovirus in a packaging cell. In one embodiment, the viral construct additionally comprises genetic elements that allow for the desired expression of a gene of interest in the host cell. Generation of the viral construct may be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. (1989) Molecular Cloning: A Laboratory Manual. Cold Spring Harbor Laboratory Press, N.Y.; Coffin et al. (997) Retroviruses. Cold Spring Harbor Laboratory Press, N.Y.; and "RNA Viruses: A Practical Approach" (Alan J. Cann, Ed., Oxford University Press, 2000).

Exemplary viral vectors include, for example, adenovirus vectors, adeno-associated virus vectors, retrovirus vectors, and lentivirus vectors. In some embodiments, viral vectors that integrate exogenous nucleic acids are used (e.g., virus other than adenoviral vectors). Exemplary types of viruses include HSV (herpes simplex virus), AAV (adeno associated virus), HIV (human immunodeficiency virus), BIV (bovine immunodeficiency virus), and MLV (murine leukemia virus). Nucleic acids may be transduced in any desired format that provides sufficiently efficient delivery levels, including in virus particles. A viral gene delivery vehicle may optionally comprise viral sequences such as a viral origin of replication or packaging signal. These viral sequences may be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al. (1983) *Cell* 33:153; Cane and Mulligan (1984) *Proc. Natl. Acad. Sci. U.S.A.* 81:6349; Miller et al. (1990) *Hum. Gene Therap.* 1:5-14; U.S. Pat. Nos. 4,405,712, 4,861,719, and 4,980,289; and PCT Publs. WO 89/02,468, WO 89/05,349, and WO 90/02,806. Numerous retroviral gene delivery vehicles may be utilized in the present invention, including for example those described in EP Pat. Publ. 0415731; PCT Publs. WO 90/07936, WO 94/03622, WO 93/25698, and WO 93/25234; U.S. Pat. No. 5,219,740; PCT. Publs. WO 93/11230 and WO 93/10218; Vile and Hart (1993) *Cancer Res.* 53:3860-3864; Vile and Hart (1993) *Cancer Res.* 53:962-967; Ram et al. (1993) *Cancer Res.* 53:83-88; Takamiya et al. (1992) *J. Neurosci. Res.* 33:493-503; Baba et al. (1993) *J. Neurosurg.* 79:729-735; U.S. Pat. No. 4,777,127; G.B. Patent No. 2,200,651; EP. Pat. Publ. 0345242; and PCT Publs. WO91/02805.

Other viral vector systems that may be used to deliver a polynucleotide of the present invention have been derived from herpes virus, e.g., Herpes Simplex Virus (U.S. Pat. No. 5,631,236 and PCT Publ. WO 00/08191), vaccinia virus (Ridgeway (1988) "Mammalian expression vectors," In: Rodriguez and Denhardt, eds. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) *Gene,* 68:1-10), and several RNA viruses. Exemplary viruses include an alphavirus, a poxivirus, an arena virus, a vaccinia virus, a polio virus, and the like. They offer several attractive features for various mammalian cells (see, for example, Friedmann (1989) *Science* 244:1275-1281; Ridgeway (1988) supra; Baichwal and Sugden (1986) supra; and Horwich et al. (1990) *J. Virol.* 64:642-650).

In some embodiments, lentiviral vectors are useful. Numerous lentiviruses suitable for use in the present invention are well known in the art. "Lentivirus" refers to a genus of retroviruses that are capable of infecting dividing and non-dividing cells. Lentiviruses may infect non-dividing cells owing to the karyophilic properties of their preintegration complex, which allow for its active import through the nucleopore. Several examples of lentiviruses include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates.

A lentiviral genome is generally organized into a 5' long terminal repeat (LTR), the gag gene, the pol gene, the env gene, the accessory genes (nef, vif, vpr, vpu) and a 3' LTR. The viral LTR is divided into three regions called U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA. The 5' and 3' LTR's serve to promote transcription and polyadenylation of the virion RNAs. The LTR contains all other cis-acting sequences necessary for viral replication. Lentiviruses have additional genes including vif, vpr, tat, rev, vpu, nef and vpx. Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins. Engineered lentiviral vectors are also known that may transduce hematopoietic stem cells and HSC lineages (see, for example, "RNA Viruses: A Practical Approach" (Alan J. Cann, Ed., Oxford University Press, (2000); O Narayan and Clements (1989) *J. Gen. Virol.* 70:1617-1639; Fields et al. (1990) Fundamental Virology, Raven Press.; Miyoshi et al. (1998) *J. Virol.* 72:8150-8157; U.S. Pat. Nos. 5,994,136, 6,013,516, 8,551,773, and 8,361,787; Evans et al. (1999) *Hum. Gene Ther.* 10:1479-1489; Case et al. (1999) *Proc. Natl. Acad. Sci. U.S.A.* 96:2988-2993; Uchida et al. (1998) *Proc. Natl. Acad. Sci. U.S.A.* 95:11939-11944; Miyoshi et al. (1999) *Science* 283:682-686; Sutton et al. (1998) *J. Virol.* 72:5781-5788).

The viral virus vectors may be psuedudotyped. A "pseudotyped" virus is a viral particle having an envelope protein that is from a virus other than the virus from which the RNA genome is derived. The envelope protein may be from a different virus. For example, an envelope protein is the vesicular stomatitis virus G (VSV G) protein or from measles virus. However, to eliminate the possibility of human infection, viruses may alternatively be pseudotyped with ecotropic envelope protein that limit infection to a specific species, such as mice or birds. For example, in one embodiment, a mutant ecotropic envelope protein is used, such as the ecotropic envelope protein 4.17 (see, for example, Powell et al. (2000) *Nat. Biotech.* 18:1279-1282).

The viral virus vectors may also be self-inactivating. For example, a "self-inactivating 3' LTR" is a 3' long terminal repeat (LTR) that contains a mutation, substitution or deletion that prevents the LTR sequences from driving expression of a downstream gene. A copy of the U3 region from the 3' LTR acts as a template for the generation of both LTR's in the integrated provirus. Thus, when the 3' LTR with an inactivating deletion or mutation integrates as the 5' LTR of the provirus, no transcription from the 5' LTR is possible. This eliminates competition between the viral enhancer/promoter and any internal enhancer/promoter. For example, a deletion in the U3 region of the 3' LTR of the vector DNA, i.e., the DNA used to produce the vector RNA may be made. Thus, during reverse transcription, this deletion is transferred to the 5' LTR of the proviral DNA. It is desirable to eliminate enough of the U3 sequence to greatly diminish or abolish altogether the transcriptional activity of the LTR, thereby greatly diminishing or abolishing the production of full-length vector RNA in transduced cells. However, it is generally desirable to retain those elements of the LTR that are involved in polyadenylation of the viral RNA, a function spread out over U3, R and U5. Accordingly, it is desirable to eliminate as many of the transcriptionally important motifs from the LTR as possible while sparing the polyadenylation determinants. The LTR may be rendered about 80%, 81%, 82%, 83%, 84%, 85%, 86%, 87%, 88%, 89%, 90%, 91%, 92%, 93%, 94%, 95% 96% 97%, 98%, to about 99% transcriptionally inactive.

Self-inactivating 3' LTRs and other viral self-inactivating methods and reagents are well known in the art (see, for example, Zufferey et al. (1998) *J. Virol.* 72:9873-9880; Miyoshi et al. (1998) *J. Virol.* 72:8150-8157; and Iwakuma et al. (1999) *Virol.* 261:120-132).

Other elements commonly found in viral vectors and generally operably linked to genes of interest in order to enhance the expression or utility of the viral vectors are well known and described further below.

c) Enhancers, Promoters, and Inducible Forms Thereof

Numerous well known genetic regulatory elements are known to control expression of a gene of interest. For example, a "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter, or other regulatory element or useful element of the vector, is in a correct functional location and/or orientation in relation to a nucleic acid sequence to regulate the sequence (e.g., control transcriptional initiation and/or expression of that sequence).

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, the 5' end of the transcription initiation site of the transcriptional reading frame is placed "downstream" of (i.e., 3' of) the chosen promoter. The spacing between promoter elements frequently is flexible, so that promoter function is preserved when elements are inverted or moved relative to one another. In the tk promoter, the spacing between promoter elements may be increased to 50 bp apart before activity begins to decline. Depending on the promoter, it appears that individual elements may function either cooperatively or independently to activate transcription.

In addition, a specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons may be either natural or synthetic. The efficiency of expression may be enhanced by the inclusion of appropriate transcription enhancer elements.

A promoter may or may not be used in conjunction with an "enhancer," which refers to a cis-acting regulatory sequence involved in the transcriptional activation of a nucleic acid sequence. Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities. Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way. For example the CMV enhancer (Karasuyama et al. (1989) *J. Exp. Med.* 169:13) may be used in combination with the chicken β-actin promoter (see, e.g., JP 1990005890-A1). Again, one of skill in the art will be able to select the appropriate enhancer based on the desired expression pattern.

A promoter may be one naturally associated with a nucleic acid sequence, as may be obtained by isolating the 5' non-coding sequences located upstream of the coding segment and/or exon. Such a promoter may be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906). Furthermore, it is contemplated the control sequences that direct transcription and/or expression of sequences within non-nuclear organelles such as mitochondria, chloroplasts, and the like, may be employed as well. Control sequences comprising promoters, enhancers and other locus or transcription controlling/modulating elements are also referred to as "transcriptional cassettes".

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. (1989) supra). The promoters employed may be constitutive, tissue-specific, cell-specific, developmental stage-specific, inducible, and/or useful under the appropriate conditions to direct high level expression of the introduced DNA segment, such as is advantageous for gene therapy or for applications such as the large-scale production of recombinant proteins and/or peptides. The promoter may be heterologous or endogenous. Use of a T3, T7 or SP6 cytoplasmic expression system is another possible embodiment. Eukaryotic cells may support cytoplasmic transcription from certain bacterial promoters if the appropriate bacterial polymerase is provided, either as part of the delivery complex or as an additional genetic expression construct. To determine whether a particular promoter is useful, a selected promoter may be tested in the construct in vitro in an HSC lineage cell and, if the promoter is capable of promoting expression of the exogenous nucleic acid at a detectable signal-to-noise ratio, it will generally be useful in accordance with the present invention. A desirable signal-to-noise ratio is one between about 10 and about 200, a more desirable signal-to-noise ratio is one 40 and about 200, and an even more desirable signal-to-noise ratio is one between about 150 and about 200. One means of testing such a promoter, described in more detail herein below, is through the use of a signal generating exogenous nucleic acid such as a reporter, like a fluorescent protein such as the green fluorescent protein (GFP).

Non-limiting examples of promoters that may be used include the promoter for ubiquitin, CMV (U.S. Pat. No. 5,168,062 and Karasuyama et al. (1989) *J. Exp. Med.* 169:13), β-actin (Gunning et al. (1987) *Proc. Natl. Acad. Sci. U.S.A.* 84:4831-4835), and pgk (U.S. Pat. Nos. 4,615, 974 and 5,104,795; Adra et al. (1987) *Gene* 60:65-74; Singer-Sam et al. (1984) *Gene* 32:409-417; and Dobson et al. (1982) *Nucl. Acids Res.* 10:2635-2637). Alternatively, the promoter may be a tissue specific promoter. Several non-limiting examples of tissue specific promoters that may be used include lck (see, for example, Garvin et al. (1988) *Mol. Cell. Biol.* 8:3058-3064 and Takadera et al. (1989) *Mol. Cell. Biol.* 9:2173-2180), myogenin (Yee et al. (1993) *Genes Dev.* 7:1277-1289), and thy 1 (Gundersen et al. (1992) *Gene* 113:207-214). In addition, promoters may be selected to allow for inducible expression of the exogenous nucleic acid.

For expressing short RNAs, such as interfering RNAs, RNA Polymerase III promoters are well known to one of skill in the art. For example, a wide range of RNA Polymerase III promoters are disclosed in Paule and White (2000) *Nucl. Acids Res.* 28:1283-1298. The definition of RNA Polymerase III promoters also include any synthetic or engineered DNA fragment that may direct RNA Polymerase III to transcribe a downstream RNA coding sequence. Suitable promoters include, but are not limited to, the U6 or HI RNA pol III promoter sequences and the cytomegalovirus promoter.

Further, viral vector promoters, such as the RNA Polymerase III (Pol III) promoter or other promoters used as part of the viral vector, may be inducible. Any suitable inducible promoter may be used with the methods of the present invention and such promoters are well known in the art (see, for example, PCT Publ. WO 2004/056964; U.S. Pat. No. 8,679,845; and U.S. Pat. Publ. 2010/0077495). Transcription-regulatory elements conferring inducibility on the promoters may be placed within the promoter region, such as between the proximal sequence element (PSE) and the transcription start site, upstream or downstream from the TATA box. Such sequences may also be placed outside the promoter, such as downstream from the end of an interfering RNA sequence. In addition, a viral vector contain 1, 2, 3, 4, 5, 6, 7, 8, 9, 10, or more of such inducibility conferring elements in order to more or less tightly regulate transcription in response to the inducing signal.

Useful inducible Pol III promoters include tetracycline responsive promoters (see, for example, Ohkawa and Taira (2000) *Hum. Gene Therap.* 11:577-585 and Meissner et al. (2001) *Nucl. Acids Res.* 29:1672-1682), operator sequences (tetO) of the *E. coli* tetracycline resistance operon (Czauderna et al. (2003) *Nucl. Acids Res.* 31:e127; Matsukura et al. (2003) *Nucl. Acids Res.* 31:e77; van de Wetering et al. (2003) *EMBO Rep.* 4:609-615; and Ohkawa et al. (2000) *Hum. Gene Ther.* 11:577-585). Many inducible promoters may be used as a cis-regulatory element and these commonly, but not necessarily, use an element that serves a landing pad function of providing a place to which a tethering factor (a sequence-specific DNA binding protein) may bind to the DNA and bring a diversification factor, fused to the tethering factor, into sufficient proximity of the coding region so that diversification of the coding region is capable of reversible regulation. A tethering factor is one that binds to the cis-regulatory element in a sequence-specific manner. In the embodiments in which LacO serves as a cis-regulatory element, the Lac repressor, LacI, may serve as the tethering factor, and its binding to the cis-regulatory element, LacO, may be regulated by isopropyl-β-D-thio-galactoside (IPTG). In the absence of IPTG, LacI binds LacO and diversification is accelerated (or otherwise regulated) by the presence of the diversification factor. IPTG may be added in the event that a halt or reduction in activity of the diversification factor is desired. In embodiments in which TetO serves as the cis-regulatory element, TetR may be a suitable tethering factor, and the activity of the diversification factor may be regulated by tetracycline or doxycycline. Other transcription-regulatory elements that allow or inducible expression are well known in the art and may be inserted into the promoter region for controlled expression of genes of interest. For example, LPTG-inducible systems based on LacO and LacI repressors are well known in the art, as are inducible systems based on Cre, GalO, MTII (phorbol ester, TFA), MMTV (glucocorticoids), beta-interferon (poly(rI) or poly(rc)), adenovirus 5 E2 (E1A), collagenase (phorbol ester, TFA), and the like. For RNA Polymerase I- or Pol LI-based transcription units, well-established inducible systems such as tetracycline transactivator systems, reverse tetracycline transactivator systems, and ecdysone systems may be used.

Additional regulatory elements are also well known that may enhance expression of the gene of interest. One type of posttranscriptional regulatory sequence is an intron positioned within the expression cassette, which may serve to stimulate gene expression. Since introns placed in such a manner may expose the RNA transcript of the gene of interest to the normal cellular splicing and processing mechanisms, it may be desirable to locate intron-containing exogenous nucleic acids in an orientation opposite to that of the vector genomic transcript. Alternatively, a method of enhancing expression of a gene of interest is through the use of a posttranscriptional regulatory element which does not rely on splicing events, such as the posttranscriptional processing element of herpes simplex virus, the posttranscriptional regulatory element of the hepatitis B virus (HPRE) or that of the woodchuck hepatitis virus (WPRE), which contains an additional cis-acting element not found in the HPRE. The regulatory element is positioned within the vector so as to be included in the RNA transcript of the exogenous nucleic acid, but outside of stop codon of the exogenous nucleic acid translational unit. The use of such regulatory elements are particularly preferred in the context of modest promoters, but may be contraindicated in the case of very highly efficient promoters.

d) Other Vector Elements

Vectors of the present invention may include a multiple cloning site (MCS), which is a nucleic acid region that contains multiple restriction enzyme sites, any of which may be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression.

The vectors useful for the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements may serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. For example, Pol III terminators preferably comprise of stretches of 4 or more thymidine ("T") residues. In a preferred embodiment, a cluster of 5 consecutive Ts is linked immediately downstream of the RNA coding region to serve as the terminator. In such a construct pol III transcription is terminated at the second or third T of the DNA template, and thus only 2 to 3 uridine ("U") residues are added to the 3' end of the coding sequence. In certain embodiments, the termination signal may be a lack of transcribable or translatable sequence, such as due to a sequence truncation.

In eukaryotic gene expression, a polyadenylation signal is generally added in order to effect proper polyadenylation of the transcript. The nature of the polyadenylation signal is not believed to be crucial to the successful practice of the invention, and any such sequence may be employed. Some examples include the SV40 polyadenylation signal or the bovine growth hormone polyadenylation signal, convenient and known to function well in various target cells. Polyadenylation may increase the stability of the transcript or may facilitate cytoplasmic transport.

In order to propagate a vector of the invention in a host cell, it may contain one or more origins of replication sites (often termed "ori"), which is a specific nucleic acid sequence at which replication is initiated. Alternatively an autonomously replicating sequence (ARS) may be employed if the host cell is yeast.

e) Virus Production and Delivery

When certain viral vectors are used, any method known in the art may be used to produce infectious viral particles, such as retroviral particles whose genome comprises an RNA copy of the viral construct described above. Preferably, the viral construct is introduced into a packaging cell line. The packaging cell line provides the viral proteins that are required in trans for the packaging of the viral genomic RNA into viral particles. The packaging cell line may be any cell line that is capable of expressing retroviral proteins. Useful packaging cell lines include 293 (ATCC CCL X), HeLa (ATCC CCL 2), D17 (ATCC CCL 183), MDCK (ATCC CCL 34), BHK (ATCC CCL-10) and Cf2Th (ATCC CRL 1430). The packaging cell line may stably express the necessary viral proteins (see, for example, U.S. Pat. No.

6,218,181). Alternatively a packaging cell line may be transiently transfected with plasmids comprising nucleic acid that encodes the necessary viral proteins. In one embodiment a packaging cell line that stably expresses the viral proteins required for packaging the RNA genome is transfected with a plasmid comprising the viral construct described above. In another embodiment a packaging cell line that does not stably express the necessary viral proteins is co-transfected with two or more plasmids (see, for example, Yee et al. (1994) *Meth. Cell. Biol.* 43A:99-112). In some embodiments, the packaging cell line may not express envelope gene products. In this case, the packaging cell line will package the viral genome into particles that lack an envelope protein. As the envelope protein is responsible, in part, for the host range of the viral particles, the viruses may be pseudotyped as described above. In other embodiments, RNA interference activity of the packaging cells may be suppressed in order to improve the production of recombinant virus. This includes, without limitation, the use of cotransfection or stable transfection of constructs expressing siRNA molecules to inhibit Dicer, an RNase III family member of ribonuclease which is essential for RNA interference (Hammond et al. (2001) *Nat. Rev. Genet.* 2:110-119). The recombinant virus is then preferably purified from the packaging cells, titered and diluted to the desired concentration according to standard protocols well known in the art.

Target cells may be transduced in any way that allows the virus to contact the target cells in which delivery of a sequence containing a gene of interest is desired according to well-known methods in the art (see, for example U.S. Pat. No. 8,552,150). In some embodiments, a suitable amount of virus is introduced into a subject directly (in vivo), for example though injection into the host's body. In some preferred embodiments, the viral particles are injected into a subject's peripheral blood stream. In other preferred embodiments, the viral particles are injected into a subject through intra-dermal injection, subcutaneous injection, intra-peritoneal cavity injection, or intra-venal injection. The virus may be delivered using a subdermal injection device, such as those disclosed in U.S. Pat. Nos. 7,241,275, 7,115, 108, 7,108,679, 7,083,599, 7,083,592, 7,047,070, 6,971,999, 6,808,506, 6,780,171, 6,776,776, 6,689,118, 6,670,349, 6,569,143, 6,494,865, 5,997,501, 5,848,991, 5,328,483, 5,279,552, 4,886,499. Other injection locations also are suitable, such as directly into organs comprising target cells. For example intra-lymph node injection, intra-spleen injection, or intra-bone marrow injection may be used to deliver virus to the lymph node, the spleen and the bone marrow, respectively. Transduced cell populations of interest may then be selected.

In other embodiments of the present invention, a suitable amount of virus is introduced into target cells obtained from a subject (ex vivo), for example through incubation of the virus with target primary cells or target cells in culture. The target cells may be cells obtained from bone marrow, fetal liver, peripheral blood, amniotic fluid, cord blood, and the like. Methods to obtain cells from a subject are well known in the art as described above. The virus may be suspended in media and added to the wells of a culture plate, tube or other container. The media containing the virus may be added prior to the plating of the cells or after the cells have been plated. Preferably cells are incubated in an appropriate amount of media to provide viability and to allow for suitable concentrations of virus in the media such that infection of the host cell occurs.

In still other embodiments, target cells are provided and contacted with the virus in vitro, such as in culture plates. The cells may be incubated with the virus for a sufficient amount of time to allow the virus to infect the cells. Preferably the cells are incubated with virus for at least 1 hour, more preferably at least 5 hours and even more preferably at least 10 hours. In ex vivo, in vitro, and in vivo delivery embodiments, any concentration of virus that is sufficient to infect the desired target cells may be used, as may be readily determined by the skilled artisan. When the target cell is to be cultured, the concentration of the viral particles is at least 1 PFU/µl, more preferably at least 10 PFU/µl, even more preferably at least 400 PFU/µl and even more preferably at least $1 \times 10^4$ PFU/µl. The titer of the virus may be adjusted to allow for, on average, 1, 2, 3, 4, 5, or more independent cellular transductions with independent viral constructs. In one embodiment, the viral titer is adjusted to allow for 1 or fewer such cellular transduction events in order to prevent multiple integration events. The methods of infecting cells disclosed above do not depend upon individual-specific characteristics of the cells. As a result, they are readily extended to all mammals.

As discussed above, the recombinant virus may be pseudotyped to confer upon it a broad host range as well as target cell specificity. One of skill in the art would also be aware of appropriate internal promoters to achieve the desired expression of a polynucleotide or gene of interest in a particular animal species. Thus, one of skill in the art will be able to modify the method of infecting dendritic cells derived from any species.

The transduced cells may be analyzed, for example for integration, transcription, and/or expression of genes of interest, the number of copies of the gene integrated, and the location of the integration. Such analysis may be carried out at any time and may be carried out by any methods known in the art. Incubator animals in which a recombinant virus or virus-infected target cells are administered may be analyzed for location of infected cells, expression of the virus-delivered gene of interest, modulation of an immune response, and/or monitored for symptoms associated with a disease or disorder by any methods known in the art.

C. Subjects and Cancer Cell Transplantation

As described above, genetically modified cancer cells, with or without genetically unmodified cancer cells, are transplanted into syngeneic subjects. Such cells are transplanted into subjects such that they proliferate, develop, and/or differentiate in an in vivo environment. The presence, absence, or strength of immunological pressure against the cancer cells in the in vivo environment is engineered based on the type of subject into which the cells are transplanted.

"Immunocompetent" subjects are those subjects comprising immune cells and immune function required to establish a normal or desired immune response following exposure to an antigen. The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. In one embodiment, the immunocompetent subject is a wild type subject having a completely intact immune system. In another embodiment, the immunocompetent subject is a wild type subject having a completely intact, yet maturing, immune system (e.g., a juvenile subject). In still another embodiment, the immunocompetent subject has an intact immune system required for mediating immune responses using a specific arm of the immune system (e.g., acquired vs. innate and/or humoral vs. cytotoxic).

"Immuno-incompetent" subjects are those subjects lacking one or more immune cell types or lacking an immune function thereof to establish a normal or desired level of at least one immune response following exposure to an antigen. Immuno-incompetent subjects are more susceptible to opportunistic infections, for example viral, fungal, protozoan, or bacterial infections, prion diseases, and certain neoplasms. "Immunodeficient" subjects are subjects in which no native host immune response may be mounted, such as is the case with severe combined immunodeficiency (SCID) mice. "Immunocompromised" subjects have at least one substantially reduced immunological function relative to immunocompetent subjects. In either case, reduction in or absence of immunological function and/or cell types can arise from many different and well known manners. For example, hematopoietic stem cells (HSCs) that give rise to all immune cells are any project thereof can be negatively affected in development, function, differentiation, survival, and the like.

HSCs are typically defined by the presence of a characteristic set of cell markers and "marker phenotyping," which refers to identification of markers or antigens on cells for determining their phenotype (e.g., differentiation state and/or cell type), is useful to describe immune cell type and function. This may be done by immunophenotyping, which uses antibodies that recognize antigens present on a cell. The antibodies may be monoclonal or polyclonal, but are generally chosen to have minimal cross reactivity with other cell markers. It is to be understood that certain cell differentiation or cell surface markers are unique to the animal species from which the cells are derived, while other cell markers will be common between species. These markers defining equivalent cell types between species are given the same marker identification even though there are species differences in structure (e.g., amino acid sequence). Cell markers include cell surfaces molecules, also referred to in certain situations as cell differentiation (CD) markers, and gene expression markers. The gene expression markers are those sets of expressed genes indicative of the cell type or differentiation state. In part, the gene expression profile will reflect the cell surface markers, although they may include non-cell surface molecules.

Marker phenotypes useful for identifying HSC are well known in the art. For human HSC, for example, the cell marker phenotypes preferably include $CD34^+$ $CD38^{-CD}90$ $(Thy1)^+$ $Lin^-$. For mouse HSCs, an exemplary cell marker phenotype is $Sca-1^+$ $CD90^+$ (see, e.g., Spangrude et al. (1988) Science 1:661-673) or $c-kit^+$ $Thy^{lo}Lin^-Sca-1^+$ (see, Uchida et al (1990) J. Clin. Invest. 101:961-966). Alternative HSC markers such as aldehyde dehydrogenase and AC133 may also be used (see, for example, Storms et al. (1999) Proc. Natl. Acad. Sci. U.S.A. 96:9118-9123 and Yin et al. (1997) Blood 90:5002-5012). The reduction or absence of cells having such marker phenotypes, for example, indicates an immunodeficient subject.

HSC are clonogenic cells, which possess the properties of both self-renewal (expansion) and multilineage potential giving rise to all types of mature blood cells, many lineages of which can give rise to defined immune response modulatory cells. HSC are responsible for hematopoiesis and undergo proliferation and differentiation to produce mature blood cells of various lineages while still maintaining their capacity for self-renewal. The ability to self-renew maintains the HSC population for the lifespan of an animal and also allows HSC to repopulate the bone marrow of lethally irradiated hosts. Early HSC development displays a hierarchical arrangement, starting from long-term (LT-) HSCs, which have extensive self-renewal capability, followed by the expansion state, which corresponds to short-term (ST-) HSCs (having limited self-renewal ability) and proliferative multipotent progenitors (MPP) (having multipotent potential but no self-renewal capability). MPP is also a stage of priming or preparation for differentiation. An MPP differentiates and, during this process, the more primitive population gives rise to a less primitive population of cells, which is unable to give rise to a more primitive population of cells. Genetic programs control these processes, including the multipotential, self-renewal, and activation (or transient amplification) of HSCs, and lineage commitment from MPP to lymphoid and myeloid progenitor cells.

Thus, HSCs give rise to committed lymphoid or myeloid progenitor cells. "Committed myeloid progenitor cells" refer to cell populations capable of differentiating into any of the terminally differentiated cells of the myeloid lineage. Encompassed within the myeloid progenitor cells are the "common myeloid progenitor cells (CMP)", a cell population characterized by limited or non-self-renewal capacity but which is capable of cell division to form granulocyte/macrophage progenitor cells (GMP) and megakaryocyte/erythroid progenitor cells (MEP). Such cell populations may then give rise to myeloid dendritic, myeloid erythroid, erythroid, megakaryocytes, granulocyte/macrophage, granulocyte, and macrophage cells. Non-self-renewing cells refers to cells that undergo cell division to produce daughter cells, neither of which have the differentiation potential of the parent cell type, but instead generates differentiated daughter cells. Committed progenitor cells of the myeloid lineage include oligopotent CMP, GMP, and MEP as defined herein, but also encompass unipotent erythroid progenitor, megakaryocyte progenitor, granulocyte progenitor, and macrophage progenitor cells. Different cell populations of myeloid progenitor cells are distinguishable from other cells by their differentiation potential, and the presence of a characteristic set of cell markers. The marker phenotypes useful for identifying CMPs include those well known in the art. For CMP cells of murine origin, for example, the cell population is characterized by the marker phenotype $c-Kit^{high}$ (CD117) $CD16^{low}$ $CD34^{low}$ $Sca-1^{neg}$ $Lin^{neg}$ and further characterized by the marker phenotypes $Fc\gamma R^{lo}$ $IL-7R\alpha^{neg}$ (CD127). The murine CMP cell population is also characterized by the absence of expression of markers that include B220, CD4, CD8, CD3, Ter119, Gr-1 and Mac-1. For CMP cells of human origin, the cell population is characterized by $CD34^+$ $CD38^+$ and further characterized by the marker phenotype, $CD123^+$ (IL-3Rα) $CD45RA^{neg}$. The human CMP cell population is also characterized by the absence of cell markers CD3, CD4, CD7, CD8, CD10, CD11b, CD14, CD19, CD20, CD56, and CD234a. Descriptions of marker phenotypes for various myeloid progenitor cells are described in, for example, U.S. Pat. Nos. 6,465,247 and 6,761,883 and Akashi (2000) Nature 404:193-197.

A committed progenitor cell of the myeloid lineage is the "granulocyte/macrophage progenitor cell (GMP)". GMP are cells derived from common myeloid progenitor cells, and characterized by a capacity to give rise to granulocyte (e.g., basophils, eosinophils, and neutrophils) and macrophage cells, but which do not typically give rise to erythroid cells or megakaryocytes of the myeloid lineage. Similar to other committed progenitor cells, GMPs lack self-renewal capacity. Murine GMPs may be characterized by the marker phenotype $c-Kit^{hi}$ (CD117) $Sca-1^{neg}Fc\gamma R^{hi}$ (CD16)

IL-7Rγ$^{neg}$CD34$^{pos}$. Murine GMPs also lack expression of markers B220, CD4, CD8, CD3, Gr-1, Mac-1, and CD90. Human GMPs may be characterized by the marker phenotype CD34$^+$ CD38$^+$ CD123+CD45RA$^+$. Human GMP cell populations are also characterized by the absence of markers CD3, CD4, CD7, CD8, CD10, CD11b, CD14, CD19, CD20, CD56, and CD235a.

"Megakaryocyte/erythroid progenitor cells (MEP)" are derived from the CMPs and are characterized by their capability of differentiating into committed megakaryocyte progenitor and erythroid progenitor cells. MEP give rise to erythroid cells and megakaryocytes, but do not typically give rise to granulocytes, macrophages, or myeloid dendritic cells. Mature megakaryocytes are polyploid cells that are precursors for formation of platelets, a developmental process regulated by thrombopoietin. Erythroid cells are formed from the committed erythroid progenitor cells through a process regulated by erythropoietin, and ultimately differentiate into mature red blood cells. Murine MEPs may be characterized by cell marker phenotype c-Kit$^{hi}$ and IL-7Rα$^{neg}$ and further characterized by marker phenotypes FcγR$^{lo}$ and CD34$^{low}$. Murine MEP cell populations may also be characterized by the absence of markers B220, CD4, CD8, CD3, Gr-1, and CD90. Another exemplary marker phenotype for mouse MEPs is c-kit$^{high}$ Sca-1$^{neg}$ Lin$^{neg/low}$ CD16$^{low}$ CD34$^{low}$. Human MEPs may be characterized by marker phenotypes CD34$^+$ CD38$^+$ CD123$^{neg}$ CD45RA$^{neg}$. Human MEP cell populations may also be characterized by the absence of markers CD3, CD4, CD7, CD8, CD10, CD11b, CD14, CD19, CD20, CD56, and CD235a.

Further restricted progenitor cells in the myeloid lineage are the granulocyte progenitor, macrophage progenitor, megakaryocyte progenitor, and erythroid progenitor cell types. "Granulocyte progenitor (GP)" cells are characterized by their capability to differentiate into terminally differentiated granulocytes, including eosinophils, basophils, and neutrophils. The GP typically do not differentiate into other cells of the myeloid lineage. "Megakaryocyte progenitor cell (MKP)" cells are characterized by their capability to differentiate into terminally differentiated megakaryocytes but generally not other cells of the myeloid lineage (see, e.g., WO 2004/024875).

For the lymphoid lineage, a "committed lymphoid progenitor cell" refers to an oligopotent or unipotent progenitor cell capable of differentiating into any of the terminally differentiated cells of the lymphoid lineage, such as T cells (e.g., CD4+ T cells, CD8+ T cells, CD4+/Foxp3+ regulatory T cells), B cells, NK cells, or lymphoid dendritic cells, but which do not typically differentiate into cells of the myeloid lineage. As with cells of the myeloid lineage, different cell populations of lymphoid progenitors are distinguishable from other cells by their differentiation potential, and the presence of a characteristic set of cell markers. Encompassed within the lymphoid progenitor cells are the "common lymphoid progenitor cells (CLP)", which are oligopotent cells characterized by a capacity to give rise to B-cell progenitors (BCP), T-cell progenitors (TCP), NK cells, and dendritic cells. These progenitor cells have little or no self-renewing capacity, but are capable of giving rise to T lymphocytes, B lymphocytes, NK cells, and lymphoid dendritic cells. The marker phenotypes useful for identifying CLPs are commonly known in the art. For CLP cells of mouse, the cell population may be characterized by the presence of markers as described in, for example, Kondo et. al., (1997) Cell 91:661-672, while for human CLPs, a marker phenotype of CD34$^+$ CD38$^+$ CD10$^+$ IL7R+ may be used (Galy et al. (1995) Immunity 3:459-473 and Akashi et al. (1999) Int. J Hematol. 69:217-226).

Numerous other suitable cell surface markers are presently known to the skilled artisan and such markers will find advantageous use in the methods and compositions described herein. For instance, several additional potential murine markers have recently been identified for the various myeloid progenitor cell populations based on array analysis of mRNA expression. See, e.g., Iwasaki-Arai et al. (2003) J Exp. Med. 197:1311-1322; Akashi et al. (2000) Nature 404:193-197; Miyamoto et al. (2002) Dev. Cell 3:137-147; Traver et al. (2001) Blood 98:627-635; Akashi et al. (2003) Blood 101:383-390; and Terskikh et al. (2003) Blood 102: 102:94-101. Based on this same type of mRNA expression analysis, additional cell surface markers such as CD110, CD114, CD116, CD117, CD127, and CD135 may also find use for isolating one or more of the identified myeloid progenitor subpopulations in humans, as described in Manz et al. (2002) Proc. Natl. Acad. Sci. U.S.A. 99:11872-11877.

Useful cells of the HSC lineage to be transduced may be capable of differentiating into cells of the myeloid lineage, i.e., granulocytes, macrophages, megakaryocytes, erythroid cells, and/or myeloid dendritic cells. These include, among others, HSCs, and committed myeloid progenitor cells CMPs, GMPs, and MEPs. These cells will have the relevant characteristics, particularly differentiation potential and cell marker characteristics described above.

HSC and related lineage cells may be mobilized from the bone marrow into the peripheral blood by prior administration of cytokines or drugs to the subject (see, e.g., Lapidot et al. (2002) Exp. Hematol. 30:973-981). The term "cytokine" refers to compounds or compositions that in the natural state are made by cells and affect physiological states of the cells that produce the cytokine (i.e., autocrine factors) or other cells. Cytokine also encompasses any compounds or compositions made by recombinant or synthetic processes, where the products of those processes have identical or similar structure and biological activity as the naturally occurring forms. Lymphokines refer to natural, synthetic, or recombinant forms of cytokines naturally produced by lymphocytes, including, but not limited to, IL-1, IL-3, IL-4, IL-6, IL-11, and the like. Cytokines and chemokines capable of inducing mobilization include, by way of example and not limitation, granulocyte colony stimulating factor (G-CSF), granulocyte macrophage colony stimulating factor (GM-CSF), erythropoietin (Kiessinger et al. (1995) Exp. Hematol. 23:609-612), stem cell factor (SCF), AMD3100 (AnorMed, Vancouver, Canada), interleukin-8 (IL-8), and variants of these factors (e.g., pegfilgastrim and darbopoietin). Combinations of cytokines and/or chemokines, such as G-CSF and SCF or GM-CSF and G-CSF, may act synergistically to promote mobilization and may be used to increase the number of HSC and progenitor cells in the peripheral blood, particularly for subjects who do not show efficient mobilization with a single cytokine or chemokine (see, for example, Morris et al. (2003) J. Haematol. 120:413-423).

Immuno-incompetent subjects can be generated in many different ways well known in the art. They can result from modulating the function and/or number of various parameters in numerous combinations. For example, immune cell populations can be targeted for modulation that are resting, mitotic, terminally differentiated, post-mitotic, unactivated, activated, and the like, in order to effect a desired immune-incompetency. "Resting" cells refer to a non-cycling cell in a non-replicative state. Although resting cells may have the ability to replicate and divide upon activation, they are quiescent since they are non-cycling. Thus, "resting" cells are not simply manipulated immune cells that have been stimulated to divide and then engineered to revert to a quiescent, non-dividing phase. Resting cells can be "naïve," which means that they are immune cells that have differentiated in bone marrow, successfully undergone positive and negative selection in the thymus, and are mature, but have not been activated and are not memory cells. Naïve T cells are commonly characterized by the surface expression of L-selectin (CD62L); the absence of the activation markers, CD25, CD44, or CD69; and the absence of memory CD45RO isoform. They also express functional IL-7 receptors, consisting of subunits IL-7 receptor-α, CD127, and common-γ chain, CD132. In the naive state, T cells are thought to be quiescent and non-dividing, requiring the common-gamma chain cytokines IL-7 and IL-15 for homeostatic survival mechanisms. By contrast, activated T cells express or up-regulate expression of surface markers, CD25, CD44, CD62L$^{low}$, and CD69 and may further differentiate into memory T cells. Naïve B cells have not been exposed to antigen since they would either become a memory B cell or a plasma cell that secretes antibodies. In one embodiment, a resting cell becomes "activated" when it is triggered to enter into a state of reproduction or doubling and may include a cell entering the cell cycle, cell division, or mitosis. In another embodiment, a resting cell may also become "activated" when it encounters an external signal, such as an antigen or a cytokine, that initiates the activity of terminally differentiated, mature immunological cells to generate an immune response (e.g., T cell or B cell function).

In one embodiment, such subjects are obtained through defined or undefined genetic modifications. Representative, non-limiting examples of such genetic modifications are described above regarding immunocompromised animals. Moreover, the term "severe combined immune deficiency (SCID)" refers to a condition characterized by absence of T cells and lack of B cell function. Common forms of SCID caused by genetic modification include: X-linked SCID which is characterized by gamma chain gene mutations in the IL2RG gene and the lymphocyte phenotype T(−) B(+) NK(−); and autosomal recessive SCID characterized by Jak3 gene mutations and the lymphocyte phenotype T(−) B(+) NK(−), ADA gene mutations and the lymphocyte phenotype T(−) B(−) NK(−), IL-7R alpha-chain mutations and the lymphocyte phenotype T(−) B(+) NK(+), CD3 delta or epsilon mutations and the lymphocyte phenotype T(−) B(+) NK(+), RAG1/RAG2 mutations and the lymphocyte phenotype T(−) B(−) NK(+), Artemis gene mutations and the lymphocyte phenotype T(−) B(−) NK(+), CD45 gene mutations and the lymphocyte phenotype T(−) B(+) NK(+). In another example, genetically modified subjects that are immunodeficient have the severe combined immunodeficiency mutation, Prkdc$^{scid}$, commonly referred to as the scid mutation (see, for example, Bosma et al. (1989) *Immunogenet.* 29:54-56). Mice homozygous for the scid mutation are characterized by an absence of functional T cells and B cells, lymphopenia, hypoglobulinemia and a normal hematopoietic microenvironment. The scid mutation may be detected, for example, by detection of markers for the scid mutation using well-known methods.

In another embodiment, such subjects are obtained through non-genetic ablation of immune cell function or numbers. Other agents can be used to ablate immune cell function or numbers. For example, they may be conditioned with sub-lethal irradiation or lethal irradiation with high frequency electromagnetic radiation. The radiation can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

Similarly, non-genetic ablation of immune cell function or numbers can be effected through treatment with a radiomimetic drug such as busulfan or nitrogen mustard. Other immune cell cytoreductive drugs, include, among others, cyclophosphamide, ifosfamide, etoposide, cytosine arabinoside, carboplatin, and other chemotherapeutic agents (Montillo et al. (2004) *Leukemia* 18:57-62; Dasgupta et al. (1996) *J. Infusional Chemother.* 6:12; and Wright et al. (2001) *Blood* 97:2278-2285). Other classes of cytoreductive drugs include, but are not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of beta-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921).

Non-genetic ablation of immune cell function or numbers can be effected through treatment with agents, such as antibodies, to deplete immune system-mediating cell populations, or treatment with agents that preferentially deplete immune system-mediating cell populations (see, for example, Hayakawa et al. (2009) *Stem Cells* 27:175-182). For example, anti-CD4 and anti-CD8 antibodies can be used to neutralize and/or deplete CD4+ T cells and CD8+ T cells, respectively. Similarly, anti-CD3 antibodies can be used to deplete all T cells, anti-B220 and/or anti-CD19 antibodies can be used to deplete all B cells, anti-CD11b antibodies can be used to deplete macrophages, anti-Ly-6G (Gr-1) antibodies can be used to deplete monocytes and granulocytes, and anti-NK1.1 antibodies can be used to deplete Natural Killer (NK) cells.

Assays for confirming immune-incompetence of one or more immune cell types or functions are also well known in the art. Determining the differentiation potential of cells, and thus the presence or absence of immune cell populations, is typically conducted by exposing the cells to conditions that permit development into various terminally differentiated cells. These conditions generally comprise a mixture of cytokines and growth factors in a culture medium permissive for development of the myeloid or lymphoid lineage. Colony forming culture assays rely on culturing the cells in vitro via limiting dilution and assessing the types of cells that arise from their continued development. A common assay of this type is based on methylcellulose medium supplemented with cytokines (e.g., MethoCult, Stem Cell Technologies, Vancouver, Canada and Kennedy et al. (1997) *Nature* 386:488-493). Cytokine and growth factor formulations permissive for differentiation in the hematopoietic pathway are described in Manz et al. (2002) *Proc. Natl. Acad. Sci. U.S.A.* 99:11872-11877; U.S. Pat. No. 6,465,249; and Akashi et al., *Nature* 404:193-197). Cytokines include SCF, FLT-3 ligand, GM-CSF, IL-3, TPO, and EPO. Another in vitro assay is long-term culture initiating cell (LTC-IC) assay, which typically uses stromal cells to support hematopoiesis (see, e.g., Ploemache et al. (1989) *Blood* 74:2755-2763 and Sutherland et al. (1995) *Proc. Natl. Acad. Sci. U.S.A.* 87:3745).

Another type of assay suitable for determining the immune-incompetence state of a subject relies upon in vivo administration of cells into a host animal and assessment of the repopulation of the hematopoietic system. The recipient is immunocompromised or immunodeficient to limit rejection and permits acceptance of allogeneic or xenogeneic cell transplants. A useful animal system of this kind is the NOD/SCID (Pflumio et al. (1996) *Blood* 88:3731; Szilvassym et al. (2002) "Hematopoietic Stem Cell Protocol" in *Methods in Molecular Medicine*, Humana Press; Greiner et al. (1998) *Stem Cells* 16:166-177; Piacibello et al. (1999) *Blood* 93:3736-3749) or Rag2 deficient mouse (Shinkai et al. (1992) *Cell* 68:855-867). Cells originating from the infused cells are assessed by recovering cells from the bone marrow, spleen, or blood of the host animal and determining presence of cells displaying specific cellular markers (i.e., marker phenotyping), typically by FACS analysis. Detection of markers specific to the transplanted cells permits distinguishing between endogenous and transplanted cells. For example, antibodies specific to human forms of the cell markers (e.g., HLA antigens) identify human cells when they are transplanted into suitable immunodeficient mouse.

Transplantation of genetically modified cancer cells, with or without genetically unmodified cancer cells, into subjects of interest may be accomplished using methods generally known in the art. For example, subjects of interest may be engrafted with the transplanted cells by various routes. Such routes include, but are not limited to, intravenous administration, subcutaneous administration, administration to a specific tissue (e.g., focal transplantation), injection into the femur bone marrow cavity, injection into the spleen, administration under the renal capsule of fetal liver, and the like. Cells may be administered in one infusion, or through successive infusions over a defined time period sufficient to generate a desired effect. Exemplary methods for transplantation, engraftment assessment, and marker phenotyping analysis of transplanted cells are well known in the art (see, for example, Pearson et al. (2008) *Curr. Protoc. Immunol.* 81:15.21.1-15.21.21; Ito et al. (2002) *Blood* 100:3175-3182; Traggiai et al. (2004) *Science* 304:104-107; Ishikawa et al. *Blood* (2005) 106:1565-1573; Shultz et al. (2005) *J. Immunol.* 174:6477-6489; and Holyoake et al. (1999) *Exp. Hematol.* 27:1418-1427).

Genetically modified cancer cells can be isolated or otherwise purified away from unmodified cancer cells. Alternatively, genetically modified cancer cells and unmodified cancer cells can be mixed together. For example, co-culturing the two types of cancer cells creates a controlled baseline such that relative overrepresentation or underrepresentation of genetically modified cancer cells relative to unmodified cancer cells in a subject indicates a growth advantage or disadvantage, respectively. The ratio of genetically modified cancer cells to unmodified cancer cells is preferably 1:1, but can modulated in any amount to determine the relative growth advantage of each cell type to the other (e.g., 1:1, 1.1:1, 1.2:1, 1.3:1, 1.4:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1, or greater).

The number of cells transplanted may be adjusted based on the desired level of engraftment in a given amount of time. Generally, $1 \times 10^5$ to about $1 \times 10^9$ cells/kg of body weight, from about $1 \times 10^6$ to about $1 \times 10^8$ cells/kg of body weight, or about $1 \times 10^7$ cells/kg of body weight, or more cells, as necessary, may be transplanted. In some embodiment, transplantation of at least about $1.0 \times 10^6$, $2.0 \times 10^6$, $3.0 \times 10^6$, $4.0 \times 10^6$, or $5.0 \times 10^6$ total cells relative to an average size mouse is effective.

Engraftment of transplanted cells may be assessed by any of various methods, such as, but not limited to, tumor volume, tumor nodule numbers, time of administration, flow cytometric analysis of cells of interest obtained from the subject at one or more time points following transplantation, and the like. For example, tumor size can be monitored and tumors of a certain size, such as being greater than 1.1, 1.2, 1.3, 1.4, 1.5, 1.6, 1.7, 1.8, 1.9, 2.0, 2.1, 2.2, 2.3, 2.4, 2.5 centimeters or larger in diameter in the longest dimension, can signal the time for tumor harvesting. Similarly, the number of clonal tumors, such as 1, 2, 3, 4, 5, 6, 7, 8, 9, 10, 11, 12, 13, 14, 15, 16, 17, 18, 19, 20 or more nodules can signal the time for tumor harvesting. Alternatively, a time-based analysis of waiting 1, 2, 3, 4, 5, 6, 7, 8, 9, 10, 11, 12, 13, 14, 15, 16, 17, 18, 19, 20, 21, 22, 23, 24, 25, 26, 27, 28 days or can signal the time for tumor harvesting. Any such metrics are variables that can be adjusted according to well-known parameters in order to determine the effect of the variable on a response to anti-cancer immunotherapy. In addition, the transplanted cells can be co-transplanted with other agents, such as cytokines, extracellular matrices, cell culture supports, and the like.

D. Anti-Cancer Immunotherapy

Anti-cancer immunotherapy is administered to subjects described herein having been transplanted with genetically modified cancer cells, with or without unmodified cancer cells, in order to determine effects of the cancer cell-based genetic modifications specifically on immune system functions, as opposed to non-immune system specific effects on the cancer cells.

The term "immunotherapy" refers to any therapy that acts by targeting immune response modulation (e.g., induction, enhancement, suppression, or reduction of an immune response). The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages. The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented. The term "promote" has the opposite meaning.

The term "immunotherapeutic agent" can include any molecule, peptide, antibody or other agent which can modulate a host immune system in response to an antigen, such as expressed by a tumor or cancer in the subject. Immunotherapeutic strategies include administration of vaccines, antibodies, cytokines, chemokines, as well as small molecular inhibitors, anti-sense oligonucleotides, and gene therapy, as described further below (see, for example, Mocellin et al. (2002) *Cancer Immunol. Immunother.* 51:583-595; Dy et al. (2002) *J. Clin. Oncol.* 20: 2881-2894).

Immunotherapies that are designed to elicit or amplify an immune response are referred to as "activation immunotherapies." Immunotherapies that are designed to reduce or suppress an immune response are referred to as "suppression immunotherapies." Any agent believed to have an immune system effect on the genetically modified transplanted cancer cells can be assayed to determine whether the agent is an immunotherapy and the effect that a given genetic modification has on the modulation of immune response. In some embodiments, the immunotherapy is cancer cell-specific. In some embodiments, immunotherapy can be "untargeted," which refers to administration of agents that do not selectively interact with immune system cells, yet modulates immune system function. Representative examples of untargeted therapies include, without limitation, chemotherapy, gene therapy, and radiation therapy.

Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

In one embodiment, immunotherapy comprises adoptive cell-based immunotherapies. Well known adoptive cell-based immunotherapeutic modalities, including, without limitation, Irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, such as expressing cytokines like GM-CSF, and/or to express tumor-associated antigen (TAA) antigens, such as Mage-1, gp-100, and the like.

In another embodiment, immunotherapy comprises non-cell-based immunotherapies. In one embodiment, compositions comprising antigens with or without vaccine-enhancing adjuvants are used. Such compositions exist in many well-known forms, such as peptide compositions, oncolytic viruses, recombinant antigen comprising fusion proteins, and the like. In still another embodiment, immunomodulatory interleukins, such as IL-2, IL-6, IL-7, IL-12, IL-17, IL-23, and the like, as well as modulators thereof (e.g., blocking antibodies or more potent or longer lasting forms) are used. In yet another embodiment, immunomodulatory cytokines, such as interferons, G-CSF, imiquimod, TNFalpha, and the like, as well as modulators thereof (e.g., blocking antibodies or more potent or longer lasting forms) are used. In another embodiment, immunomodulatory chemokines, such as CCL3, CCL26, and CXCL7, and the like, as well as modulators thereof (e.g., blocking antibodies or more potent or longer lasting forms) are used. In another embodiment, immunomodulatory molecules targeting immunosuppression, such as STAT3 signaling modulators, NFkappaB signaling modulators, and immune checkpoint modulators, are used.

The term "immune checkpoint" refers to a group of molecules on the cell surface of CD4+ and/or CD8+ T cells that fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, HHLA2, butyrophilins, and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein.

"Anti-immune checkpoint therapy" refers to the use of agents that inhibit immune checkpoint nucleic acids and/or proteins. Inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and anti-CTLA-4 antibodies, either alone or in combination, are used to inhibit immune checkpoints.

In still another embodiment, immunomodulatory drugs, such as immunocytostatic drugs, glucocorticoids, cytostatics, immunophilins and modulators thereof (e.g., rapamycin, a calcineurin inhibitor, tacrolimus, ciclosporin (cyclosporin), pimecrolimus, abetimus, gusperimus, ridaforolimus, everolimus, temsirolimus, zotarolimus, etc.), hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a pyrimidine synthesis inhibitor, leflunomide, teriflunomide, a folic acid analog, methotrexate, anti-thymocyte globulin, anti-lymphocyte globulin, thalidomide, lenalidomide, pentoxifylline, bupropion, curcumin, catechin, an opioid, an IMPDH inhibitor, mycophenolic acid, myriocin, fingolimod, an NF-xB inhibitor, raloxifene, drotrecogin alfa, denosumab, an NF-xB signaling cascade inhibitor, disulfiram, olmesartan, dithiocarbamate, a proteasome inhibitor, bortezomib, MG132, Prol, NPI-0052, curcumin, genistein, resveratrol, parthenolide, thalidomide, lenalidomide, flavopiridol, non-steroidal anti-inflammatory drugs (NSAIDs), arsenic trioxide, dehydroxymethylepoxyquinomycin (DHMEQ), I3C(indole-3-carbinol)/DIM(di-indolmethane) (13C/DIM), Bay 11-7082, luteolin, cell permeable peptide SN-50, IKBa.-super repressor overexpression, NF Kappa Beta decoy oligodeoxynucleotide (ODN), or a derivative or analog of any thereo, are used. In yet another embodiment, immunomodulatory antibodies or protein are used. For example, antibodies that bind to CD40, Toll-like receptor (TLR), OX40, GITR, CD27, or to 4-1BB, T-cell bispecific antibodies, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CD11 antibody, efalizumab, an anti-CD18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA4-Ig fusion protein, abatacept, belatacept, an anti-CTLA4 antibody, ipilimumab, tremelimumab, an anti-eotaxin 1 antibody, bertilimumab, an anti-a4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an IL-1 receptor antagonist, anakinra, an anti-IL-5 antibody, mepolizumab, an IgE inhibitor, omalizumab, talizumab, an IL-12 inhibitor, an IL-23 inhibitor, ustekinumab, and the like.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion," as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

Combinations of any immunotherapeutic agent class or specific agent are also contemplated for use according to the present invention. In addition, the immunotherapy can be administered concurrently with, before, or after the transplantation of the cancer cells. The amount of immunotherapeutic agent administered is not particularly limited and is a variable whose effect on immunomodulation can be assayed. Generally, the amount of immunotherapeutic agent administered is titrated to not eliminate the transplanted cancer cells and to allow those cancer cells with a growth advantage or disadvantage to propagate or be eliminated, respectively. For solid tumors, such an amount increases infiltration of lymphocytes into the solid tumor without eliminating the tumor.

E. Immunomodulation Screening

The present invention provides an in vivo method of identifying a cancer cell modulator of response to an anti-cancer immunotherapy, comprising: a) obtaining at least a first population of cancer cells, wherein the cancer cells are syngeneic to a first and second subject, wherein the first subject is immunocompetent and the second subject is immunodeficient; b) obtaining at least a second population of cancer cells, wherein the at least first population of cancer cells are genetically engineered to comprise at least one genetic modification; c) transplanting a portion of the second population of cancer cells into the first subject; d) administering at least one immunotherapy to the first subject; e) determining the representation of the at least one genetic modification from at least one population of cancerous cells propagated in the first subject from said transplanted portion of the second population of cancer cells relative to the representation of the at least one genetic modification from the portion of the second population of cancer cells prior to transplantation; f) repeating steps c) through e) with the second subject; and g) determining at least one genetic modification having a significantly modulated relative representation in the first subject and not having a significantly modulated relative representation in the second subject, thereby identifying a cancer cell modulator of response to an anti-cancer immunotherapy.

As described above, the genetically modified cancer cells, with or without unmodified cells, are transplanted into an appropriate subject and allowed to grow and propagate in the presence of at least one immunotherapy. At a desired point, the grown and propagated genetically modified cancer cells, with or without unmodified cells, are analyzed to determine the relative representation of the genetic modifications, with or without the relative representation of unmodified cells, as compared with the population of cancer cells prior to transplantation. Achievement of a desired "response" due to the immunotherapy determines the point at which the comparison is made. The term "response" refers to an effect on transplanted cancer cell physiology, such as growth, metastasis, signaling, death, and the like. For example, tumor size, time after cancer cell transplantation, tumor location, and the like can be used to determine a response.

The term "resistance" refers to an acquired or natural resistance of cancer cells to the immunotherapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., p<0.05) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

In one embodiment, the therapeutic effect or amount of an immunotherapy on a desired outcome for the transplanted cancer cells is an endpoint. The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

Similarly, "unresponsiveness" can be a measurable endpoint. Immune cells rather than transplanted cancer cells are analyzed and the term includes refractivity of immune cell stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

At a desired endpoint, the relative representation of the at least one genetic modification from at least one population of cancerous cells propagated in the first subject from said transplanted portion of the second population of cancer cells relative to the representation of the at least one genetic modification from the portion of the second population of cancer cells prior to transplantation is determined. The end point can be based on any desired criteria, such as days after transplantation (e.g., 1, 2, 3, 4, 5, 6, 7, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or longer, or any range in between, inclusive), tumor diameter (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 cm, or larger, or any range in between, inclusive, in the longest dimension), percentage or volume of a cell sample (e.g., 0.001%, 0.01%, 0.1%, 1%, 5%, 10%, or more, or any range in between, inclusive).

In one embodiment, the cells are isolated from the subject. The term "isolated" refers to a product, compound, or composition which is separated from at least one other product, compound, or composition with which it is associated in its naturally occurring state, whether in nature or as made synthetically. In other embodiments, "isolated" means that desired cells are physically separated from other cell populations. Methods for the enrichment, purification, and/or isolation of marker phenotyped cells are disclosed herein and are also well known in the art, such as by using fluorescence-activated cell scanning (FACS), magnetic cell sorting, and centrifugation (see, for example, U.S. Pat. Nos. 5,474,687, 5,677,136, and 6,004,743; and U.S. Pat. Publ. 2001/0039052).

For example, the grown and propagated genetically modified cancer cells may be subjected to selection, purification, and/or isolation, which may include both positive and negative selection methods, to obtain an enriched or substantially pure population of cells. As used herein, "enriched" means that the percentage of marker phenotyped cells relative to other cells in a population is increased. In one embodiment, "purified" means that the percentage of marker phenotyped cells is substantially pure and excludes cells that are not marker phenotyped. A "substantially pure cell population" refers to a population of cells having a specified cell marker characteristic and differentiation potential that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or more, or any value or range in between, of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that do not display a specified marker characteristic and differentiation potential under designated assay conditions.

In one embodiment, fluorescence activated cell sorting (FACS), also referred to as flow cytometry, is used to sort and analyze the different cell populations. Cells having a cellular marker or other specific marker of interest are tagged with an antibody, or typically a mixture of antibodies, that bind the cellular markers. Each antibody directed to a different marker is conjugated to a detectable molecule, particularly a fluorescent dye that may be distinguished from other fluorescent dyes coupled to other antibodies. A stream of tagged or "stained" cells is passed through a light source that excites the fluorochrome and the emission spectrum from the cells detected to determine the presence of a particular labeled antibody. By concurrent detection of different fluorochromes, also referred to in the art as multicolor fluorescence cell sorting, cells displaying different sets of cell markers may be identified and isolated from other cells in the population. Other FACS parameters, including, by way of example and not limitation, side scatter (SSC), forward scatter (FSC), and vital dye staining (e.g., with propidium iodide) allow selection of cells based on size and viability. FACS sorting and analysis of HSC and related lineage cells is well known in the art and described in, for example, U.S. Pat. Nos. 5,137,809; 5,750,397; 5,840,580; 6,465,249; Manz et al. (202) Proc. Natl. Acad. Sci. U.S.A. 99:11872-11877; and Akashi et al. (200) Nature 404:193-197. General guidance on fluorescence activated cell sorting is described in, for example, Shapiro (2003) Practical Flow Cytometry, 4th Ed., Wiley-Liss (2003) and Ormerod (2000) Flow Cytometry: A Practical Approach, 3rd Ed., Oxford University Press.

Another method of isolating useful cell populations involves a solid or insoluble substrate to which is bound antibodies or ligands that interact with specific cell surface markers. In immunoadsorption techniques, cells are contacted with the substrate (e.g., column of beads, flasks, magnetic particles, etc.) containing the antibodies and any unbound cells removed. Immunoadsorption techniques may be scaled up to deal directly with the large numbers of cells in a clinical harvest. Suitable substrates include, by way of example and not limitation, plastic, cellulose, dextran, polyacrylamide, agarose, and others known in the art (e.g., Pharmacia Sepharose 6 MB macrobeads). When a solid substrate comprising magnetic or paramagnetic beads is used, cells bound to the beads may be readily isolated by a magnetic separator (see, e.g., Kato and Radbruch (1993) Cytometry 14:384-92). Affinity chromatographic cell separations typically involve passing a suspension of cells over a support bearing a selective ligand immobilized to its surface. The ligand interacts with its specific target molecule on the cell and is captured on the matrix. The bound cell is released by the addition of an elution agent to the running buffer of the column and the free cell is washed through the column and harvested as a homogeneous population. As apparent to the skilled artisan, adsorption techniques are not limited to those employing specific antibodies, and may use nonspecific adsorption. For example, adsorption to silica is a simple procedure for removing phagocytes from cell preparations.

FACS and most batch wise immunoadsorption techniques may be adapted to both positive and negative selection procedures (see, e.g., U.S. Pat. No. 5,877,299). In positive selection, the desired cells are labeled with antibodies and removed away from the remaining unlabeled/unwanted cells. In negative selection, the unwanted cells are labeled and removed. Another type of negative selection that may be employed is use of antibody/complement treatment or immunotoxins to remove unwanted cells.

It is to be understood that the purification or isolation of cells also includes combinations of the methods described above. A typical combination may comprise an initial procedure that is effective in removing the bulk of unwanted cells and cellular material, for example leukapharesis. A second step may include isolation of cells expressing a marker common to one or more of the progenitor cell populations by immunoadsorption on antibodies bound to a substrate. An additional step providing higher resolution of different cell types, such as FACS sorting with antibodies to a set of specific cellular markers, may be used to obtain substantially pure populations of the desired cells.

In some embodiments, control populations are isolated and/or used for a relative comparison. The term "control" refers to any reference standard suitable to provide a comparison to expression products, such as DNA barcode tags, of interest in the test sample. In one embodiment, the control comprises obtaining a "control sample" from which expression product levels are detected and compared to the expression product levels from the test sample. Such a control sample may comprise any suitable sample, including but not limited to cells that were co-cultured with the genetically engineered cells and co-administered or otherwise grown and analyzed in parallel (e.g., in vitro to simulate a scenario of a lack of immune pressure relative to the in vivo grown genetically engineered cells). In another embodiment, a control can comprise a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of experiments or patients, such as a set of cancer patients, or for a set of cancer patients receiving a certain treatment, or for a set of patients with one outcome versus another outcome. In the former case, the specific expression product level of each experiment or patient can be assigned to a percentile level of expression, or expressed as either higher or lower than the mean or average of the reference standard expression level. In another preferred embodiment, the control may comprise normal cells, cells from independent experiments or patients treated with a certain therapy such as combination immunotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The genetically engineered and/or control cells of interest can then be analyzed to determine the effects of immunotherapy thereon according to well-known methods in the art. In one embodiment, relative growth rates or other ratios (e.g., absence, presence, change in increase, change in decrease, etc.) of cells can be determined as a measure of immunotherapy effect on a population of cells of interest. For example, local co-administration of genetically unengineered and genetically engineered cells into a host animal to form a tumor and subsequent analysis of the relative representation of genetically engineered cells to genetically unengineered cells in the tumor as compared with the ratio at administration or other relevant time point is an indicator of whether the genetic perturbation resulted in increased, decreased, or no effect on the cell to immunotherapy. Such relative measurements can also be made in relation to genetically engineered cells themselves. For example, the relative representation of cells harboring a given genetic perturbation prior to transplantation can be determined directly (e.g., by sequencing the genetic perturbation itself) or indirectly (e.g., by sequencing a tag associated with the genetic perturbation or otherwise detecting a marker associated with the genetic perturbation or cell comprising the genetic perturbation). The representation can then be determined at a later point in time after cell transplantation and immunotherapy and changes therein indicate whether the genetic perturbation resulted in increased, decreased, or no effect on the cell to immunotherapy. Combining such analyses with various immunocompetent and immuno-incompetent systems further allows for the identification of which particular compartments of the immune system mediate any observed immunological effect.

In another embodiment, immune responses are analyzed to determine the effects of immunotherapy on the genetically engineered and/or control cells of interest according to well-known endpoints and metrics and as described above regarding immunotherapies. For example, modulation of angiogenesis, metastasis, disease remission, disease relapse, tumor recurrence, death, autoimmunity, allergy (e.g., asthma, atopic dermatitis, allergic conjunctivitis, pollen allergy, food allergy, etc.), vaccination response, immunotolerance, immune exhaustion, immunological memory, immunological epitope responses, cytokine responses, and the like can be analyzed and associated with genetic perturbations and/or specific immune compartments.

Methods for determining relative representation of cells, genetic perturbations, and/or other immunologic effects are well known in the art. For example, determination of target nucleic acid sequences of interest can be performed using variety of sequencing methods known in the art. In preferred embodiments, a particular genetic perturbation is characterized by a measure of a nucleic acid or product thereof (e.g., mRNA). Marker expression may be monitored in a variety of ways, including by detecting mRNA levels, protein levels, or protein activity, any of which may be measured using standard techniques. Detection may involve quantification of the level of gene expression (e.g., genomic DNA, cDNA, mRNA, protein, or enzyme activity), or, alternatively, may be a qualitative assessment of the level of gene expression, in particular in comparison with a control level. The type of level being detected will be clear from the context. Various amplification and detection methods may also be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR), real time PCR, NASBA, Q-beta amplification, target-mediated amplification, ligase chain reaction, self-sustained sequence replication (SSR), transcription amplification, and the like. Many techniques are known in the state of the art for determining absolute and relative levels of gene expression, commonly used techniques suitable for use in the present invention include in situ hybridization, microarray, chip array, serial analysis of gene expression (SAGE), Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In certain embodiments, nucleic acid detection can be accomplished using methods including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan® reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (U.S. Ser. No. 12/027,039, filed Feb. 6, 2008; Porreca et al. (2007) *Nat. Methods* 4:931), polymerized colony (POLONY) sequencing (U.S. Pat. Nos. 6,432,360, 6,485,944 and 6,511,803, and PCT/US05/06425); nanogrid rolling circle sequencing (ROLONY) (U.S. Ser. No. 12/120,541, filed May 14, 2008), allele-specific oligo ligation assays (e.g., oligoligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., on cyclic array sequencing using platforms such as Roche 454, Illumina Solexa or MiSeq or HiSeq, AB-SOLiD, Helicos, Polonator platforms and the like, can also be utilized. High-throughput sequencing methods are described in U.S. Ser. No. 61/162,913, filed Mar. 24, 2009. A variety of light-based sequencing technologies are known in the art (Landegren et al. (1998) *Genome Res.* 8:769-76; Kwok (2000) *Pharmocogenom.* 1:95-100; and Shi (2001) *Clin. Chem.* 47:164-172) (see, for example, U.S. Pat. Publ. Nos. 2013/0274117, 2013/0137587, and 2011/0039304).

Similarly, polypeptides and/or cells of interest can be distinguished according to many well-known methods in the art including, but not limited to, flow cytometry, fluorescence activated cell sorting (FACS), fluorescence microscopy, detectable cell barcode technology (U.S. Pat. Publ. 2011/0263457), immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., "Basic and Clinical Immunology," Sites and Terr, eds., Appleton and Lange, Norwalk, Conn. Pp. 217-262, 1991, which is incorporated by reference). Preferred are binder-ligand immunoassay methods including reacting antibodies with an epitope or epitopes and competitively displacing a labeled polypeptide or derivative thereof.

For any factor or metric analyzed herein, a "significant change" refers to value that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more, or any range in between, inclusive, different from a reference value. In one embodiment, the reference value is a positive control, a metric at a given point in time, or a metric associated with a specific sample type or state. For example, the top 10% of genetically engineered loci or wild type genes thereof can be selected or the top 10% of genetic changes in a given tested cell line can be selected. In another embodiment, "significant change" can refer to stratification based on standard deviations from a mean, such as greater than or less than 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, or more, or any range in between, inclusive. In some embodiments, the reference value is "pre-determined" such as with a control value. For example, a pre-determined biomarker amount and/or activity measurement(s) may be determined in populations of experiments, patients, and the like, such as cell lines of a particular cancer. The pre-determined biomarker amount and/or activity measurement(s) can be a single number or the pre-determined biomarker amount and/or activity measurement(s) can vary according to specific parameters, such as time, sample, cell line, and the like.

In some embodiments, combinatorial analyses are further conducted. The term "synergistic effect" refers to the combined effect of two or more cancer cell-associated factors that modulate anti-cancer immunity that is greater than effects of each individual factor alone.

The present invention further pertains to novel agents identified by the above-described screening assays. Accordingly, it is within the scope of this invention to further use an agent identified as described herein in an appropriate animal model. For example, an agent identified as described herein may be used in an animal model to determine the efficacy, toxicity, or side effects of treatment with such an agent. Alternatively, an agent identified as described herein may be used in an animal model to determine the mechanism of action of such an agent. Furthermore, this invention pertains to uses of novel agents identified for prophylactic, diagnostic, screening, and therapeutic purposes.

EXEMPLIFICATION

This invention is further illustrated by the following examples, which should not be construed as limiting.

Example 1: In Vivo Identification of Cancer-Associated Targets for Immunotherapy by a Genetically Manipulated, Transplantable Cancer Model There is a great need in the art to identify physiologically relevant cancer-associated factors that mediate suppression of anti-tumor immunity as targets for immunotherapy. It has been discovered herein that such physiologically relevant cancer-associated factors can be identified using methods harnessing in vivo immune pressure forces upon genetically modified cancer cells.

Specific methods used during the investigation are described below. Specifically, inducible Cas9-expressing cell lines were initially created. MC38 colon carcinoma, Lewis lung carcinoma, and BP melanoma cell lines were infected with a lentivirus that expresses Cas9 under a doxycycline-inducible promoter along with blasticidin resistance as a selectable marker. Five days after infection, cells were selected in blasticidin and the resistant population was single cell sorted into 96-well plates by limiting dilution. Individual clones were tested for Cas9 expression by culturing cells in 1 ug/mL doxycycline for 48 hours and followed by Western blotting for 3×FLAG-tagged Cas9 using an anti-FLAG antibody. Clones with the highest induced expression of Cas9 were chosen for subsequent use.

Target cells to be infected were plated to achieve 60-70% confluence prior to lentiviral infection. Lentivirus encoding the genetic perturbation (i.e., open reading frame, tumor-associated mutation, or sgRNA) was added to cells in media containing 5 ug/ml polybrene. Forty-eight hours after infection cells were selected in puromycin.

Doxycycline was added to virally transduced cells at 1 ug/mL for 7 days to induce Cas9 expression and knockout of target genes. After doxycycline induction, cells were cultured for three days in DMEM with 10% tetracycline-free FBS to downregulate Cas9 expression.

Genetically-modified cells were identified using cell surface markers and flow cytometry. Prior to implantation, tumor cells were modified by lentiviral transduction to express a phenotypic marker, Thy1.1, truncated human CD19, GFP, or tdTomato. In single gene experiments, these markers were used to differentiate populations at time of tumor harvest by flow cytometric detection of GFP or tdTomato or fluorescent antibody conjugates to Thy1.1 or truncated CD19.

Cells were then transplanted. For example, cells were washed out of cell culture media and resuspended in Hank's balanced salt solution (HBSS). Subcutaneous tumors were initiated in C57BL6/J mice by injecting 1 million cells in a volume of 0.2 ml into the right flank. Tumors growth took between 14-28 days and mice were sacrificed when tumors reach >=2 cm in diameter in the longest dimension.

The animals were also treated with immunotherapy. In particular, B16 melanoma expressing GMCSF and a dominant negative milk fat globule EGF 8 (B16/GMCSF/RGE) were harvested, washed, and resuspended in HBSS. Cells were subsequently irradiated at a dose of 3500 rads. After washing and resuspension in HBSS, $5 \times 10^5$ cells in a volume of 0.2 ml were injected subcutaneously on the abdomen of a wild type C57BL6/J animal known in the art as GVAX vaccination. This GVAX vaccination was administered on day 0 (day of tumor implantation) and day +3.

Mice were also treated with a monoclonal antibody directed at mouse CD8 (mAb: 53-6.7; BioXcell) 100 ug in 0.1 ml injected intraperitoneally on days −2, −1, 0, and then every 3-4 days following tumor implantation. At the time of tumor harvest, CD8 depletion was confirmed by flow cytometric staining of splenocytes with mouse anti-CD8 recognizing an alternate epitope.

Extracted tumors were mechanically dissociated by grinding tumor tissue in a 6 well plate. Tumor tissue was then resuspended in ACK lysing buffer for red blood cell lysis for 2 minutes at room temperature. Tissue was then digested in a solution of collagenase/DNase for 20 minutes on a shaker at 37° C. Collagenase/DNase is inactivated and cells were resuspended in 0.25% trypsin for 5 minutes at 37° C. in a water bath.

Genomic DNA from the input cell population or the resulting single cell suspension from tumor harvest was extracted using DNEasy® Blood and Tissue DNA isolation kit (Qiagen). Amplification of the sgRNA barcode region from gDNA or barcoded ORF was performed by the Genetic Pertubations Platform (Broad Institute) and the amplified regions were sequenced using an Illumina MiSeq or HiSeq platform.

The methods described herein relate to an in vivo model for immunotherapy target discovery that selectively applies immune pressure to genetically modified cancer cells. A schematic diagram of one embodiment of the methods described herein are shown in FIG. 1. The methods have been validated with cancer cells expressing known immune inhibitory genes or gene deletions (FIGS. 2-5). As described above, genetic modifications besides alterations of known immune inhibitory genes or gene deletions are contemplated and compatible with the methods described herein, such as, without limitation, RNAi gene knockdown, CRISPR/Cas9-mediated gene deletion or targeted mutagenesis, overexpression of mutant alleles, and the like. Large numbers of genetic modifications can be screened simultaneously, allowing for rapid therapeutic target discovery.

Figure 6:
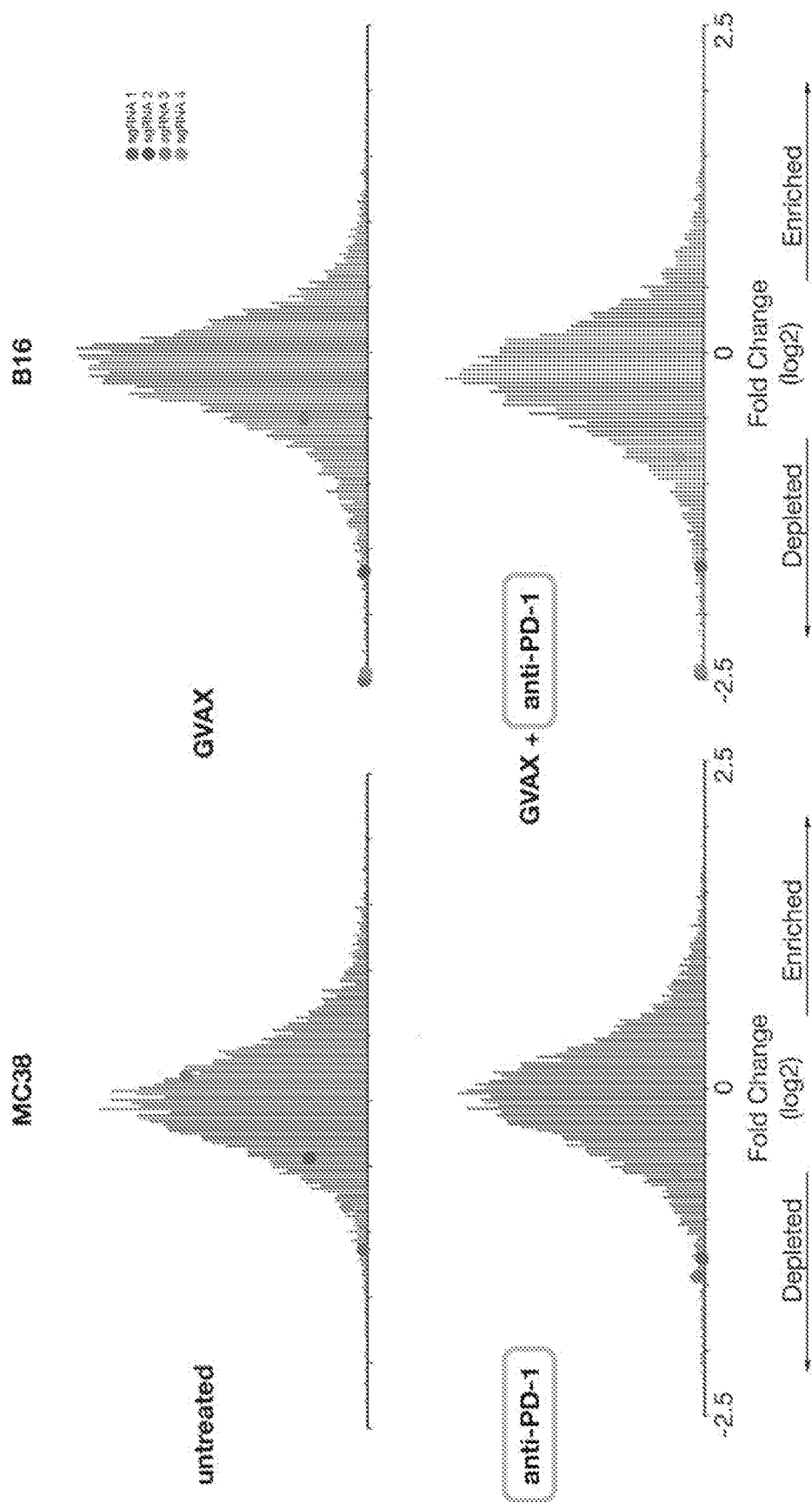
FIG. 6 shows that sgRNAs targeting CD47 are selectively depleted in anti-PD-1 treated mouse tumors relative to tumors growing in TCRalpha KO mice.
Figure 7:
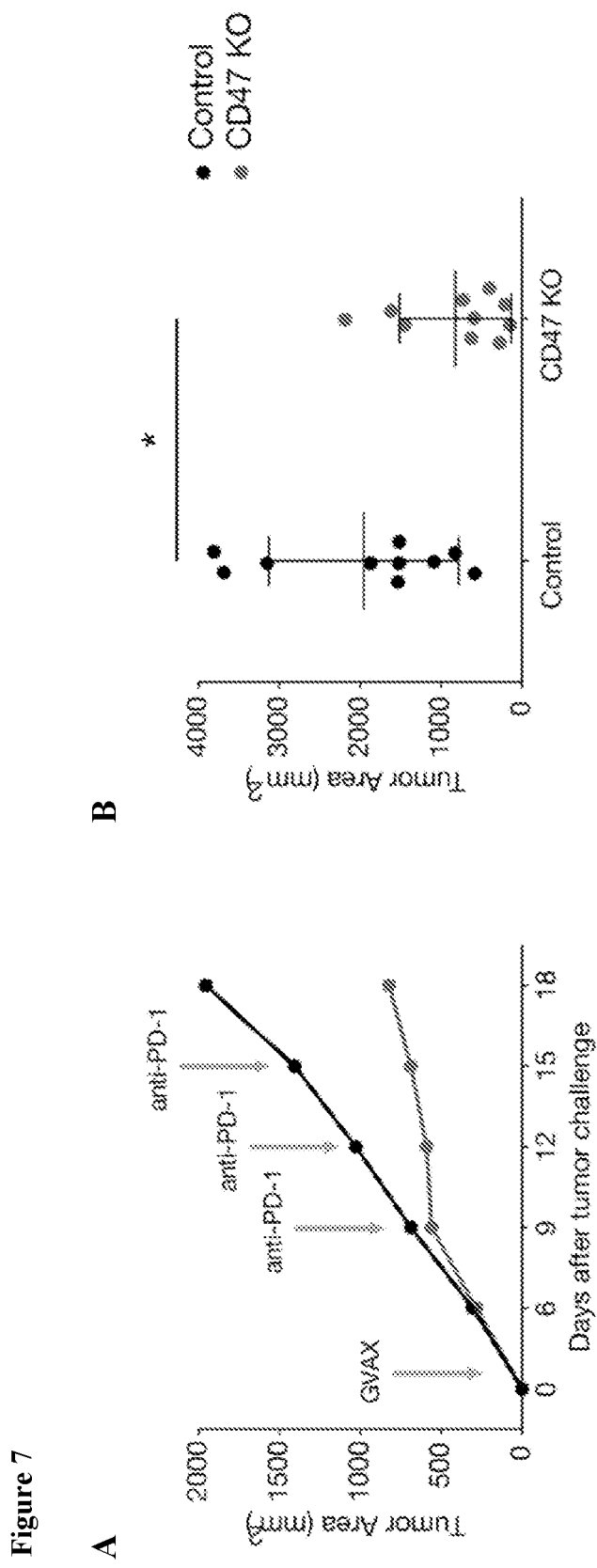
FIG. 7 includes 2 panels, identified as panels A and B, which show that loss of CD47 improves therapeutic response to anti-PD-1 treatment in B16 melanoma as measured by tumor growth over time (Panel A) and at day 18 (Panel B).

For example, sgRNAs targeting CD47 were determined to be selectively depleted in anti-PD-1-treated mouse tumors relative to tumors growing in TCRalpha knockout (KO mice). In particular, B16 melanoma cells were transfected with either CD47 sgRNA or control sgRNA and assayed for loss of CD47 by flow cytometry. The sequences of the sgRNA used are the following: CD47 sgRNA 1 (5'-TATAGAGCTGAAAAACCGCA-3') (SEQ ID NO: 1), CD47 sgRNA 2 (5'-CCACATTACGGACGATGCAA-3') (SEQ ID NO: 2), CD47 sgRNA 3 (5'-TCTTACGAGGAG-GAGAAAGG-3') (SEQ ID NO: 3), and CD47 sgRNA 4 (5'-GCAAGTGTAGTTTCCCACCA-3') (SEQ ID NO: 4), and control sgRNA (5'-AAAAAGTCCGCGATTACGTC-3') (SEQ ID NO: 5). CD47 KO cells were sorted to purity by FACS. Two cohorts of mice were then implanted with either CD47 KO B16 cells or control sgRNA cells and vaccinated with B16 Gvax cells on day 1 (1 million irradiated B16-GMCSF cells/mouse). All mice were then treated with anti-PD-1 (clone 29f.1a12) on days 9, 12, and 15. Tumor volume was measured every 3 days started at day 6 until day 18. Three out of four guide RNAs targeting CD47 (i.e., CD47 sgRNA numbers 1, 2, and 4) in a pool of 10 thousand individual guide RNAs were selectively depleted in conditions where T cells are present relative to TCRalpha KO control tumors in MC38 and B16 cell lines (FIG. 6). In addition, the loss of CD47 improves therapeutic response to anti-PD-1 treatment in B16 melanoma (FIG. 7).

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. An in vivo method of identifying a cancer cell modulator of response to an anti-cancer immunotherapy, comprising the steps in order:
   a) obtaining at least a first population of cancer cells, wherein the cancer cells are syngeneic to a first and second subject, wherein the first subject is immuno-competent and the second subject is immuno-incompetent;
   b) obtaining at least a second population of cancer cells from the first population of cancer cells, wherein the at least second population of cancer cells are genetically engineered to comprise at least one genetic modification;
   c) transplanting a portion of the second population of cancer cells into the first subject;
   d) administering at least one immunotherapy to the first subject;

e) determining the representation of the at least one genetic modification from at least one population of cancerous cells propagated in the first subject from said transplanted portion of the second population of cancer cells relative to the representation of the at least one genetic modification from the portion of the second population of cancer cells prior to transplantation;

f) repeating steps c) through e) with the second subject; and g) determining at least one genetic modification having a significantly modulated relative representation in the first subject and not having a significantly modulated relative representation in the second subject, thereby identifying a cancer cell modulator of response to an anti-cancer immunotherapy;

wherein the at least one immunotherapy inhibits an anti-immune checkpoint selected from the group consisting of CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, HHLA2, butyrophilins, A2aR, and combinations thereof;

wherein the immune-incompetent second subject comprises at least one substantially reduced immunological function of at least one immune cell type relative to the immunocompetent first subject or wherein the immune-incompetent second subject is immunodeficient;

wherein the at least one immune cell type is contacted with an agent that substantially reduces the at least one immunological function of the at least one immune cell type;

and wherein the agent is selected from the group consisting of an antibody, radiation, and chemotherapy.

2. The method of claim 1, wherein
a) the first population of cancer cells is solid tumor cancer cells;
b) the first population of cancer cells is hematological cancer cells;
c) the first population of cancer cells is autologous to the first or second subject;
d) the first population of cancer cells is human cancer cells;
e) the first and second subject is a vertebrate; or
f) the first subject is a wild-type non-human animal.

3. The method of claim 1, wherein
a) the at least one immune cell type is selected from the group consisting of B cells, T cells, CD8+ T cells, CD4+ T cells, regulatory T cells, macrophages, granulocytes, Natural Killer (NK) cells, and combinations thereof;
b) the at least one immune cell type is selected from the group consisting of resting, mitotic, terminally differentiated, post-mitotic, unactivated, and activated cells, and combinations thereof; or
c) the at least one immune cell type has not been exogenously stimulated to divide.

4. The method of claim 1, wherein the at least first population of cells is contacted with a vector comprising an exogenous nucleic acid, wherein the vector 1) integrates into a chromosome or 2) exists as an extrachromosomal nucleic acid compartment of the cell, and expresses exogenous nucleic acids or proteins in the cell to generate the at least one genetic modification in the at least second population of cancer cells, wherein a) a cell of the at least second population of cancer cells has a single vector comprising an exogenous nucleic acid, b) the single vector is inducible, c) the single vector is inducible using a doxycycline-inducible promoter, and d) the single vector comprises a nucleic acid encoding a reporter.

5. The method of claim 4, wherein the vector is a viral vector.

6. The method of claim 4, wherein the exogenous nucleic acid comprised within the vector is selected from the group consisting of a nucleic acid barcode, an open reading frame, a tumor-associated mutation, mRNA, sgRNA, antisense RNA, shRNA, siRNA, microRNA, PiwiRNA, an engineered, non-naturally occurring Clustered Regularly Interspaced Short Palindromic Repeats (CRISPR) guide RNA that hybridizes with a target nucleic acid sequence of interest or a nucleotide sequence encoding a Type-II Cas9 protein.

7. The method of claim 4, wherein the reporter a) is a fluorescent protein or a cell-surface protein and b) is used to identify and/or isolate the genetically modified cancer cells in the at least second population of cancer cells.

8. The method of claim 1, wherein the portion of the second population of cancer cells consists essentially of the genetically modified cancer cells; and
a) is focally transplanted to the first and/or second subject or
b) is systemically transplanted to the first and/or second subject.

9. The method of claim 1, wherein the at least one immunotherapy reduces but does not eliminate the portion of the second population of cancer cells.

10. The method of claim 1, wherein the at least one immunotherapy increases infiltration of lymphocytes into a solid tumor formed by the portion of the second population of cancer cells.

11. The method of claim 1, wherein the relative representation of the at least one genetic modification is determined by detecting nucleic acid markers, protein markers, and/or cellular markers of the cells comprising the at least one genetic modification, optionally wherein the markers are detected by nucleic acid sequencing, next generation sequencing, flow cytometry, and immunodetection.

12. The method of claim 1, wherein a significant modulation in relative marker representation is at least a 1.5-fold difference.

13. The method of claim 1, wherein the at least first population of cancer cells and the at least second population of cancer cells are co-cultured and the at least second population of cancer cells comprises at least a portion of the at least first population of cancer cells.

14. The method of claim 13, wherein said at least second population of cancer cells has essentially an equal ratio of genetically modified and genetically unmodified cancer cells.

15. The method of claim 13, wherein a significant modulation in relative marker representation is at least a 1.5-fold difference.

16. The method of claim 2, wherein the vertebrate is selected from the group consisting of a mammal, a non-human primate, a mouse, a rat, and a zebrafish.

17. The method of claim 5, wherein the viral vector is a) a lentiviral vector.

18. An in vivo method of identifying a cancer cell modulator of response to an anti-cancer immunotherapy, comprising the steps in order:
a) obtaining at least a first population of cancer cells, wherein the cancer cells are syngeneic to a first and second subject, wherein the first subject is immunocompetent and the second subject is immuno-incompetent;

b) obtaining at least a second population of cancer cells from the first population of cancer cells, wherein the at least second population of cancer cells are genetically engineered to comprise at least one genetic modification;

c) transplanting a portion of the second population of cancer cells into the first subject;

d) administering at least one immunotherapy to the first subject;

e) determining the representation of the at least one genetic modification from at least one population of cancerous cells propagated in the first subject from said transplanted portion of the second population of cancer cells relative to the representation of the at least one genetic modification from the portion of the second population of cancer cells prior to transplantation;

f) repeating steps c) through e) with the second subject; and g) determining at least one genetic modification having a significantly modulated relative representation in the first subject and not having a significantly modulated relative representation in the second subject, thereby identifying a cancer cell modulator of response to an anti-cancer immunotherapy;

wherein the at least one immunotherapy inhibits an anti-immune checkpoint selected from the group consisting of PD-1, PD-L1, PD-L2, CTLA-4, and combinations thereof; and wherein a significant modulation in relative marker representation is at least a 1.5-fold difference.

19. The method of claim 18, wherein
a) the first population of cancer cells is solid tumor cancer cells;
b) the first population of cancer cells is hematological cancer cells;
c) the first population of cancer cells is autologous to the first or second subject;
d) the first population of cancer cells is human cancer cells;
e) the first and second subject is a vertebrate;
f) the first subject is a wild-type non-human animal; or
g) the immune-incompetent second subject comprises at least one substantially reduced immunological function of at least one immune cell type relative to the immunocompetent first subject or wherein the immune-incompetent second subject is immunodeficient.

20. The method of claim 19, wherein the immune-incompetent second subject comprises at least one substantially reduced immunological function of at least one immune cell type relative to the immunocompetent first subject or wherein the immune-incompetent second subject is immunodeficient, wherein the at least one immune cell type is contacted with an agent that substantially reduces the at least one immunological function of the at least one immune cell type, wherein the agent is selected from the group consisting of an antibody, radiation, and chemotherapy.

21. The method of claim 20, wherein
a) the at least one immune cell type is selected from the group consisting of B cells, T cells, CD8+ T cells, CD4+ T cells, regulatory T cells, macrophages, granulocytes, Natural Killer (NK) cells, and combinations thereof;
b) the at least one immune cell type is selected from the group consisting of resting, mitotic, terminally differentiated, post-mitotic, unactivated, and activated cell, and combinations thereof; or
c) the at least one immune cell type has not been exogenously stimulated to divide.

22. The method of claim 18, wherein the at least first population of cells is contacted with a vector comprising an exogenous nucleic acid, wherein the vector 1) integrates into a chromosome or 2) exists as an extrachromosomal nucleic acid compartment of the cell, and expresses exogenous nucleic acids or proteins in the cell to generate the at least one genetic modification in the at least second population of cancer cells, wherein a) a cell of the at least second population of cancer cells has a single vector comprising an exogenous nucleic acid, b) the single vector is inducible, c) the single vector is inducible using a doxycycline-inducible promoter, and d) the single vector comprises a nucleic acid encoding a reporter.

23. The method of claim 22, wherein the vector is a viral vector.

24. The method of claim 22, wherein the exogenous nucleic acid comprised within the vector is selected from the group consisting of a nucleic acid barcode, an open reading frame, a tumor-associated mutation, mRNA, sgRNA, antisense RNA, shRNA, siRNA, microRNA, PiwiRNA, an engineered, non-naturally occurring Clustered Regularly Interspaced Short Palindromic Repeats (CRISPR) guide RNA that hybridizes with a target nucleic acid sequence of interest and/or b) a nucleotide sequence encoding a Type-II Cas9 protein.

25. The method of claim 22, wherein the reporter a) is a fluorescent protein or a cell-surface protein and b) is used to identify and/or isolate the genetically modified cancer cells in the at least second population of cancer cells.

26. The method of claim 18, wherein the portion of the second population of cancer cells consists essentially of the genetically modified cancer cells;
a) is focally transplanted to the first and/or second subject or
b) is systemically transplanted to the first and/or second subject.

27. The method of claim 18, wherein the at least one immunotherapy reduces but does not eliminate the portion of the second population of cancer cells.

28. The method of claim 18, wherein the at least one immunotherapy increases infiltration of lymphocytes into a solid tumor formed by the portion of the second population of cancer cells.

29. The method of claim 18, wherein the relative representation of the at least one genetic modification is determined by detecting nucleic acid markers, protein markers, and/or cellular markers of the cells comprising the at least one genetic modification, optionally wherein the markers are detected by nucleic acid sequencing, next generation sequencing, flow cytometry, and immunodetection.

30. The method of claim 18, wherein the at least first population of cancer cells and the at least second population of cancer cells are co-cultured and the at least second population of cancer cells comprises at least a portion of the at least first population of cancer cells.

31. The method of claim 30, wherein said at least second population of cancer cells has essentially an equal ratio of genetically modified and genetically unmodified cancer cells.

32. The method of claim 19, wherein the vertebrate is selected from the group consisting of a mammal, a non-human primate, a mouse, a rat, and a zebrafish.

33. The method of claim 23, wherein the viral vector is a lentiviral vector.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 1
tatagagctg aaaaaccgca                                               20

<210> SEQ ID NO 2
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 2
ccacattacg gacgatgcaa                                               20

<210> SEQ ID NO 3
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 3
tcttacgagg aggagaaagg                                               20

<210> SEQ ID NO 4
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 4
gcaagtgtag tttcccacca                                               20

<210> SEQ ID NO 5
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 5
aaaaagtccg cgattacgtc                                               20
```